Figure 3:
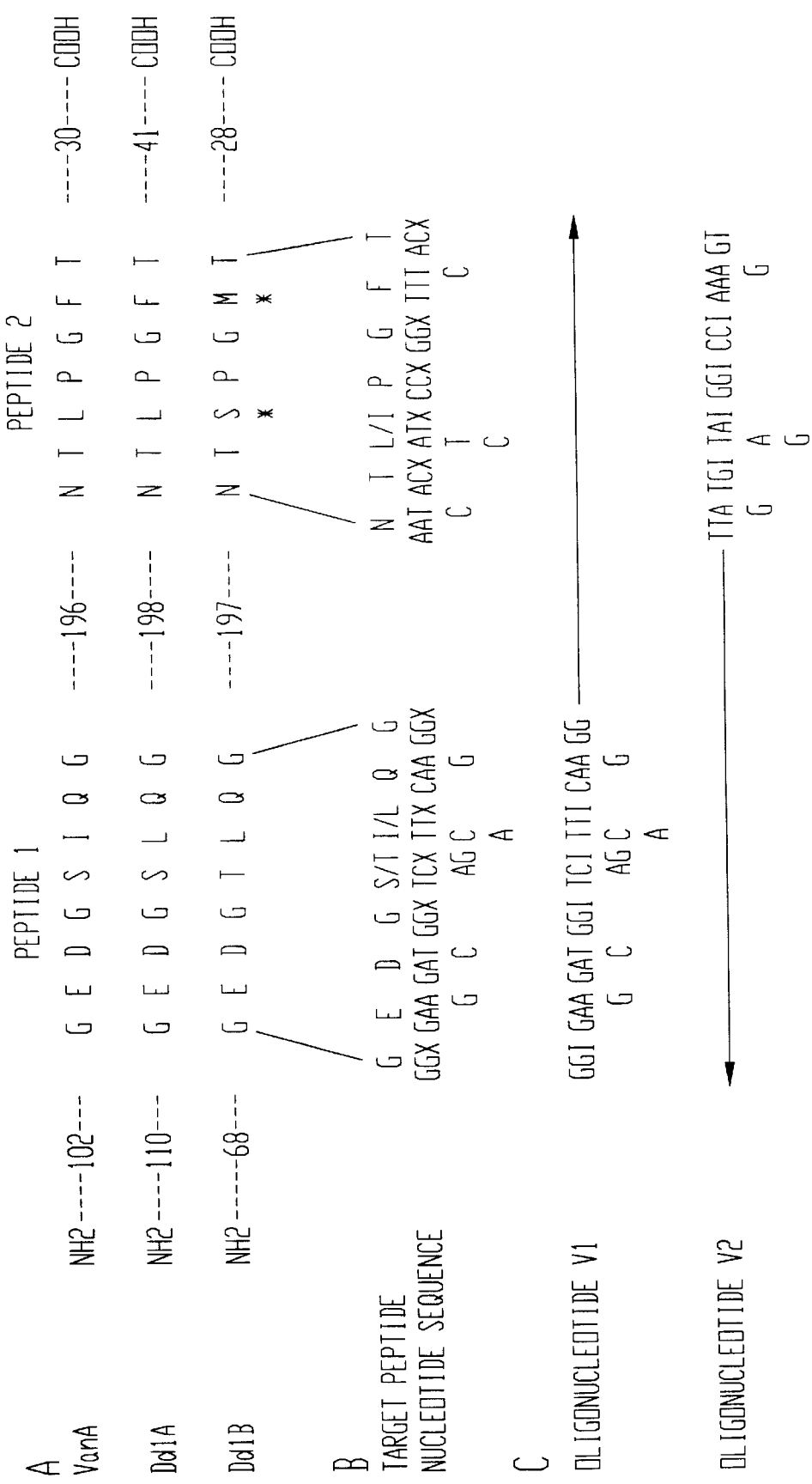

United States Patent [19]
Arthur et al.

[11] Patent Number: 5,770,361
[45] Date of Patent: Jun. 23, 1998

[54] PROTEIN CONFERRING AN INDUCIBLE RESISTANCE TO GLYCOPEPTIDES, PARTICULARLY IN GRAM-POSITIVE BACTERIA

[75] Inventors: Michel Arthur, Paris; Sylvie Dutka-Malen, Fresnes; Stefan Evers, Paris; Patrice Courvalin, Paris, all of France

[73] Assignee: Institut Pasteur, Paris Cedex, France

[21] Appl. No.: 454,196
[22] PCT Filed: Dec. 17, 1993
[86] PCT No.: PCT/FR93/01264
   § 371 Date: Sep. 7, 1995
   § 102(e) Date: Sep. 7, 1995
[87] PCT Pub. No.: WO94/14961
   PCT Pub. Date: Jul. 7, 1994

[30] Foreign Application Priority Data

Dec. 18, 1992 [FR] France .................................... 92 15671
Jul. 7, 1993 [FR] France .................................... 93 08356

[51] Int. Cl.$^6$ ............................ C12Q 1/68; C07H 21/04; C07H 21/02; C07K 15/28
[52] U.S. Cl. ........................... 435/6; 435/91.2; 435/91.1; 435/7.1; 435/7.2; 435/7.32; 435/70.21; 435/320.1; 435/69.1; 424/130.1; 424/141.1; 424/150.1; 424/192.1; 424/185.1; 536/23.7; 536/23.1; 536/24.3; 536/24.32; 530/300; 530/350

[58] Field of Search ................................... 536/23.1, 24.3, 536/24.32, 23.7; 435/91.2, 91.1, 6, 7.1, 7.2, 7.32, 70.21, 69.1, 320.1, 71.1; 424/130.1, 141.1, 150.1, 192.1, 185.1; 530/300, 350

[56] References Cited

PUBLICATIONS

Bowie et al. Science 247: 1306–1310 1990.

Dutka Malen et al. Gene 112: 53–58 1992.

Dutka Malen et al.Mol. Gen.364–367 1990.

Al–Obeid et al. FEMS Microbiol. Letts 70:101–106 1990.

*Primary Examiner*—W. Gary Jones
*Assistant Examiner*—Dianne Rees
*Attorney, Agent, or Firm*—Oblon, Spivak, McClelland, Maier & Neustadt, P.C.

[57] ABSTRACT

The invention relates to a protein VanB involved, in Gram-positive bacteria, in resistance to glycopeptides, particularly to vancomycine, said resistance being of the type inducible by the vancomycine and non-inducible by teicoplanine. The invention also relates to the utilisation of fragments of nucleotides of the gene van B for the detection of resistances to glycopeptides.

32 Claims, 7 Drawing Sheets

```
                                                                    RBS
GAGCGTGTGCTGCGAGATACCACAGAAAACAATCAGAATTGTCTTAACTTTGAAAGGAGT         60

M  N  K  I  K  V  A  I  I  F  G  G  C  S  E  E  H  D          18
TTACAGCATGAATAAAATAAAAGTCGCAATTATCTTCGGCGGTTGCTCGGAGGAACATGA        120

V  S  V  K  S  A  I  E  I  A  A  N  I  N  T  E  K  F  D  P       38
TGTGTCGGTAAAATCCGCAATAGAAATTGCTGCGAACATTAATACTGAAAAATTCGATCC        180

H  Y  I  G  I  T  K  N  G  V  W  K  L  C  K  K  P  C  T  E    58
GCACTACATCGGAATTACAAAAAACGGCGTATGGAAGCTATGCAAGAAGCCATGTACGGA        240

W  E  A  D  S  L  P  A  I  F  S  P  D  R  K  T  H  G  L  L    78
ATGGGAAGCCGATAGTCTCCCCGCCATATTCTCCCCGGATAGGAAAACGCATGGTCTGCT        300
         primer 1
    V  M  K  E  R  E  Y  E  T  R  R  I  D  V  A  F  P  V  L  H       98
TGTCATGAAAGAAAGAGAATACGAAACTCGGCGTATTGACGTGGCTTTCCCGGTTTTGCA        360

G  K  C  G  E  D  G  A  I  Q  G  L  F  E  L  S  G  I  P  Y      118
TGGCAAATGCGGGGAGGATGGTGCGATACAGGGTCTGTTTGAATTGTCTGGTATCCCCTA        420

V  G  C  D  I  Q  S  S  A  A  C  M  D  K  S  L  A  Y  I  L      138
TGTAGGCTGCGATATTCAAAGCTCCGCAGCTTGCATGGACAAATCACTGGCCTACATTCT        480

T  K  N  A  G  I  A  V  P  E  F  Q  M  I  E  K  G  D  K  P      158
TACAAAAAATGCGGGCATCGCCGTCCCCGAATTTCAAATGATTGAAAAAGGTGACAAACC        540

E  A  R  T  L  T  Y  P  V  F  V  K  P  A  R  S  G  S  S  F      178
GGAGGCGAGGACGCTTACCTACCCTGTCTTTGTGAAGCCGGCACGGTCAGGTTCGTCCTT        600
```

*FIG. 1A*

```
G  V  T  K  V  N  S  T  E  E  L  N  A  A  I  E  A  A  G  Q        198
TGGCGTAACCAAAGTAAACAGTACGGAAGAACTAAACGCTGCGATAGAAGCAGCAGGACA       660

Y  D  G  K  I  L  I  E  Q  A  I  S  G  C  E  V  G  C  A  V     218
ATATGATGGAAAAATCTTAATTGAGCAAGCGATTTCGGGCTGTGAGGTCGGCTGCGCGGT       720

M  G  N  E  D  D  L  I  V  G  E  V  D  Q  I  R  L  S  H  G        238
CATGGGAAACGAGGATGATTTGATTGTCGGCGAAGTGGATCAAATCCGGTTGAGCCACGG      780

I  F  R  I  H  Q  E  N  E  P  E  K  G  S  E  N  A  M  I  I        258
TATCTTCCGCATCCATCAGGAAAACGAGCCGGAAAAAGGCTCAGAGAATGCGATGATTAT      840

V  P  A  D  I  P  V  E  E  R  N  R  V  Q  E  T  A  K  K  V        278
CGTTCCAGCAGACATTCCGGTCGAGGAACGAAATCGGGTGCAAGAAACGGCAAAGAAAGT      900
                    primer 2
   Y  R  V  L  G  C  R  G  L  A  R  V  D  L  F  L  Q  E  D  G     298
ATATCGGGTGCTTGGATGCAGAGGGCTTGCTCGTGTTGATCTTTTTTTGCAGGAGGATGG      960

G  I  V  L  N  E  V  N  T  L  P  G  F  T  S  Y  S  R  Y  P     318
CGGCATCGTTCTAAACGAGGTCAATACCCTGCCCGGTTTTACATCGTACAGCCGCTATCC      1020

R  M  A  A  A  A  G  I  T  L  P  A  L  I  D  S  L  I  T  L        338
ACGCATGGCGGCTGCCGCAGGAATCACGCTTCCCGCACTAATTGACAGCCTGATTACATT      1080

A  I  E  R  *                                                      342
GGCGATAGAGAGGTGACCCGTATGGAAAATGGTTTTTTGTTTTTTAGATGAAATGTTGCA      1140 amorce 1: 5' ATGGGAAGCCGATAGTC 3'  pos. 241-258 amorce 2: 5' GATTTCGTTCCTCGACC 3'  pos. 860-877 (reverse-complementary)
```

*FIG. 1B*

```
VanA    MNRIKVAILF  GGCSEEHDVS  VKSAIEIAAN  INKEKYEPLY  IGITKSGVWK  MCEKPCAEWE  NDNCYSAVLS  PDKKMHGLLV  KKNHEYEIN-  ------HVD   92
VanB    MNKIKVAIIF  GGCSEEHDVS  VKSAIEIAAN  INTEKFDPHY  IGITKNGVWK  LCKKPCTEWE  AD-SLPAIFS  PDRKTHGLLV  MKEREYETR-  ------RID   91
VanC    --MKKIAVLF  GGNSPEYSVS  LTSAASVIQA  IDPLKYEVMI  IGIAPTMDWY  WYQGNLANVR  NDIWLEDHKN  CHQLIFSSQG  FILGEKRI--  ------VPD   89
EfDdl   ---LKIILLY  GGRSEEHDVS  VLSAYSVLNA  IYYKYYQVQL  VFISKDGGWV  KGPLLSERPQ  NKEVLHLTWA  QTPEETGEFS  GKRISPSEIY  E-----EEA   91
EcDdlA  MEKLRVGIVF  GGKSAEHEVS  LQSAKNIVDA  IDKSRFDVVL  LGIDKQGQWH  VSDASNYLLN  ADDPAHIALR  PSATSLAQVP  GKHEHQLIDA  QNGQPLPTVD 100
StDdlA  MAKLRVGIVF  GGKSAEHEVS  LQSAKNIVDA  IDKIRFDVVL  LGIDKAGQWH  VNDAENYLQN  ADDPAHIALR  PSAISLAQVP  GKHQHQLINA  QNGQPLPTVD 100
EcDdlB  -MTDKIAVLL  GGTSAEREVS  LNSGAAVLAG  LREGGIDAYP  VDPKEVDVTQ  LKSM------  ----------  ----------  ----------  ------GFQ  56
        I CII      IIII CIICC  CI   I  I   C          C           IC          C C                                              
                   CC CCC     IIII II   C IC  C        C          
                                       domain 1

VanA    VAFSALHGKS  GEDGSIQGLF  ELSGIPFVGC  DIQSSAICMD  KSLTYIVAKN  AGIATPAFWV  INKDDR----  ------PVAAT  FTYPVFVKPA  RSGSSFGVKK 183
VanB    VAFPVLHGKC  GEDGAIQGLF  ELSGIPYVGC  DIQSSAACMD  KSLAYILTKN  AGIAVPEFQM  IEKGDK----  ------PEART  LTYPVFVKPA  RSGSSFGVTK 182
VanC    VLFPVLHGKY  GEDGCIQGLL  ELMNLPYVGC  HVAASALCMN  KWLHQLADT   MGIASAPTLL  LSRYENDPAT  ID--RFIQD    HGFPIFIKPN  EAGSSKGITK 186
EfDdl   IVFPVLHGPN  GEDGSIQGFM  ETINMPYVGA  GVLASANAMD  KIMTKVLLQI  VGIPQVPFVP  VLRSDWKGNP  KEVIEKCEGS   LIYPVFVKPA  NMGSSVGISK 191
EcDdlA  VIFPIVHGTL  GEDGSLQGML  RVANLPFVGS  DVLASAACMD  KDVTKRLLRD  AGLNIAPFIT  LTRANRHNIS  FA--EVESK    LGLPLFVKPA  NQGSSVGVSK 197
StDdlA  VIFPIVHGTL  GEDGSLQGML  RVANLPFVGS  DVLSSAACMD  KDVAKRLLRD  AGLNIAPFIT  LIRTNRHAFS  FA--EVESR    LGLPLFVKPA  NQGSSVGVSK 197
EcDdlB  KVFIALHGRG  GEDGTLQGML  ELMGLPYTGS  GVMASALSMD  KLRSKLLWQG  AGLPVAPWVA  LTRAEFEKGL  SDKQLAEISA   LGLPVIVKPS  REGSSVGMSK 156
                              CI  I  I    C           C           IC          C C                                ICCCII   III IC I
                                       domain 2
```

FIG. 2A

```
VanA    VNSADELDYA  IESARQYDSK  ILIEQAVSGC  EVGCAVLGNS  AALVVGEVDQ  IRLQYGIFRI  HQEVEPEKGS  ENAVITVPAD  LSAEERGRIQ  ETAKKIYKAL   283
VanB    VNSTEELNAA  IEAAGQYDGK  ILIEQAISGC  EVGCAVMGNE  DDLIVGEVDQ  IRLSHGIFRI  HQENEPEKGS  ENAMIIVPAD  IPVEERNRVQ  ETAKKVYRVL   282
VanC    VTDKTALQSA  LTTAFAYGST  VLIQKAIAGI  EIGCGILGNE  -QLTIGACDA  ISLVDGFFDF  EEKYQLIS-   --ATIIVPAP  LPLALESQIK  EQAQLLYRNL   281
EfDdl   VENRDELQEA  LEEAFRYDAR  AIVEQGIEAR  EIEVAILGNE  -DVRTILPGE  VVKDVAFYDY  DAKYINNI--  --IEMQIPAH  VPEEVAHQAQ  EYAKKAYIML   286
EcDdlA  VTSEEQYAIA  VDLAFEFDHK  VIVEQGIKGR  EIECAVLGND  -NPQASICGE  IVLTSDFYAY  DTKYIDEDG-  --AKVVVPAA  IAPEINDKIR  AIAVQAYQIL   293
StDdlA  VANEAQYQQA  VALAFEFDHK  VVVEQGIKGR  EIECAVLGND  -NPQASICGE  IVLNSEFYAY  DTKYIDDNG-  -AQVVVPAQ   IPSEVNDKIR  AIAIQAYQIL   293
EcDdlB  VVAENALQDA  LRLAFQHDEE  VLIEKWLSGP  EFTVAILGEE  ----ILPSIR  IQPSGIFYDY  EAKYLSDE-   ---IQYFCPAG LEASQEANLQ  ALVLKAWTIL   248
              I   I  IC      I                  CC  CC C  C  IC  CCCI      C                 C              II   C
                                           domain 3

VanA    GCRGLARVDM  FLQDNGRIVL  NEVNTILPGFT SYSRYPRMMA  AAGIALPELI  DRLIVIALKG  ---------                                      343
VanB    GCRGLARVDL  FLQEDGGIVL  NEVNTILPGFT SYSRYPRMAA  AAGITLPALI  DSLITLAIER  ---------                                      342
VanC    GLTGLARIDF  FVINQGAIYL  NEINTMPGFT  GHSRYPAMMA  EVGLSYEILV  EQLIALAEED  KR-------                                      343
EfDdl   DGSGLSRCDF  FLTSKNELFL  NELNIMPGFT  PFSMYPLLWE  NMGLKYSDLI  EELIQLALNR  FK-------                                      348
EcDdlA  GCAGMARVDV  FLTPENEVVI  NEINTLPGFT  NISMYPKLWQ  ASGLGYTDLI  TRLIELALER  HAANNALKIT M                                   364
StDdlA  GCAGMARVDV  FLTADNEVVI  NEINTLPGFT  NISMYPKLWQ  ASGLGYTDLI  SRLIELALER  HTANNALKIT M                                   364
EcDdlB  GCKGWGRIDV  MLDSDGQFYL  LEANTSPGMI  SHSLVPMAAR  QAGMSFSQLV  VRILELAD--  ---------                                      306
           I  IC  CC      CC     I  IIICI      I   I          IC   IC   CC II
                                        domain 4
```

FIG. 2B

```
                   RBS          L  K  I  I  L  L  Y  G  G  R     10
AAAGACAGGAAAGAAACTAGGAGGACAAGCATTTGAAGATTATTTTGTTGTATGGCGGCA     60

S  E  E  H  D  V  S  V  L  S  A  Y  S  V  L  N  A  I  Y  Y   30
GAAGTGAAGAGCACGATGTGTCTGTTTTGTCTGCATATTCCGTTTTAAATGCAATCTATT   120

K  Y  Y  Q  V  Q  L  V  F  I  S  K  D  G  Q  W  V  K  G  P   50
ATAAATATTATCAAGTACAGTTAGTCTTTATTAGTAAAGACGGTCAATGGGTAAAAGGCC   180

L  L  S  E  R  P  Q  N  K  E  V  L  H  L  T  W  A  Q  T  P   70
CTCTTTTATCTGAACGACCACAAAATAAAGAAGTTTTACATTTAACTTGGGCACAAACAC   240

E  E  T  G  E  F  S  G  K  R  I  S  P  S  E  I  Y  E  E  E   90
CTGAAGAAACAGGCGAATTTTCAGGAAAACGAATCAGTCCTTCGGAAATTTATGAAGAAG   300

A  I  V  F  P  V  L  H  G  P  N  G  E  D  G  T  I  Q  G  F   110
AAGCGATTGTTTTCCCTGTTTTACATGGGCCAAATGGTGAAGATGGAACAATTCAAGGAT   360

M  E  T  I  N  M  P  Y  V  G  A  G  V  L  A  S  V  N  A  M   130
TCATGGAAACCATTAATATGCCTTATGTAGGCGCGGGTGTCTTAGCTAGCGTTAACGCAA   420

D  K  I  M  T  K  Y  L  L  Q  T  V  G  I  P  Q  V  P  F  V   150
TGGACAAAATCATGACGAAATATCTTTTACAAACTGTTGGCATTCCACAAGTACCATTCG   480

P  V  L  R  S  D  W  K  G  N  P  K  E  V  F  E  K  C  E  G   170
TGCCAGTTTTAAGAAGTGACTGGAAAGGAAATCCAAAAGAAGTCTTTGAAAAATGTGAAG   540
```

*FIG. 4A*

```
  S   L   I   Y   P   V   F   V   K   P   A   N   M   G   S   S   V   G   I   S    190
GTTCTTTAATTTATCCGGTCTTTGTTAAACCTGCCAATATGGGTTCTAGTGTCGGAATTA                         600

K   V   E   N   R   E   E   L   Q   E   A   L   E   E   A   F   R   Y   D   A    210
GCAAAGTGGAAAATCGTGAAGAATTGCAAGAAGCATTGGAAGAAGCTTTCCGTTATGATG                         660

R   A   I   V   E   Q   G   I   E   A   R   E   I   E   V   A   I   L   G   N    230
CCCGAGCAATTGTTGAACAAGGGATCGAAGCACGTGAAATTGAAGTAGCCATTTTAGGAA                         720

E   D   V   R   T   T   L   P   G   E   V   V   K   D   V   A   F   Y   D   Y    250
ATGAAGATGTCCGTACGACTTTACCTGGTGAAGTGGTGAAAGATGTCGCTTTCTATGATT                         780

D   A   K   Y   I   N   N   T   I   E   M   Q   I   P   A   H   V   P   E   E    270
ATGATGCAAAATACATCAATAACACGATTGAAATGCAAATCCCAGCGCATGTTCCAGAAG                         840

V   A   H   Q   A   Q   E   Y   A   K   K   A   Y   I   M   L   D   G   S   G    290
AAGTAGCTCATCAAGCGCAAGAATACGCTAAAAAAGCGTATATTATGTTAGATGGAAGTG                         900

L   S   R   C   D   F   F   L   T   S   K   N   E   L   F   L   N   E   L   N    310
GCTTAAGTCGCTGTGATTTCTTCTTAACAAGCAAAAACGAATTATTCCTGAATGAATTGA                         960

T   M   P   G   F   T   D   F   S   M   Y   P   L   L   W   E   N   M   G   L    330
ACACCATGCCTGGTTTTACTGACTTTAGTATGTATCCTTTACTGTGGGAAAATATGGGCT                         1020

K   Y   S   D   L   I   E   E   L   I   Q   L   A   L   N   R   F   K   *        348
TGAAATACAGTGATTTAATTGAGGAACTGATTCAGTTAGCTTTGAATCGTTTTAAATAA                          1079
```

*FIG. 4B*

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 1140 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 68..1093

( x i ) SEQUENCE DESCRIPTION: SEQ ID NO:1:

```
GAGCGTGTGC  TGCGAGATAC  CACAGAAAAC  AATCAGAATT  GTCTTAACTT  TGAAAGGAGT              60

TTACAGC ATG AAT AAA ATA AAA GTC GCA ATT ATC TTC GGC GGT TGC TCG                    109
        Met Asn Lys Ile Lys Val Ala Ile Ile Phe Gly Gly Cys Ser
         1               5                   10

GAG GAA CAT GAT GTG TCG GTA AAA TCC GCA ATA GAA ATT GCT GCG AAC                    157
Glu Glu His Asp Val Ser Val Lys Ser Ala Ile Glu Ile Ala Ala Asn
 15                  20                  25                  30

ATT AAT ACT GAA AAA TTC GAT CCG CAC TAC ATC GGA ATT ACA AAA AAC                    205
Ile Asn Thr Glu Lys Phe Asp Pro His Tyr Ile Gly Ile Thr Lys Asn
                 35                  40                  45
```

```
GGC  GTA  TGG  AAG  CTA  TGC  AAG  AAG  CCA  TGT  ACG  GAA  TGG  GAA  GCC  GAT         253
Gly  Val  Trp  Lys  Leu  Cys  Lys  Lys  Pro  Cys  Thr  Glu  Trp  Glu  Ala  Asp
              50                  55                            60

AGT  CTC  CCC  GCC  ATA  TTC  TCC  CCG  GAT  AGG  AAA  ACG  CAT  GGT  CTG  CTT         301
Ser  Leu  Pro  Ala  Ile  Phe  Ser  Pro  Asp  Arg  Lys  Thr  His  Gly  Leu  Leu
              65                  70                            75

GTC  ATG  AAA  GAA  AGA  GAA  TAC  GAA  ACT  CGG  CGT  ATT  GAC  GTG  GCT  TTC         349
Val  Met  Lys  Glu  Arg  Glu  Tyr  Glu  Thr  Arg  Arg  Ile  Asp  Val  Ala  Phe
         80                  85                            90

CCG  GTT  TTG  CAT  GGC  AAA  TGC  GGG  GAG  GAT  GGT  GCG  ATA  CAG  GGT  CTG         397
Pro  Val  Leu  His  Gly  Lys  Cys  Gly  Glu  Asp  Gly  Ala  Ile  Gln  Gly  Leu
95                       100                      105                      110

TTT  GAA  TTG  TCT  GGT  ATC  CCC  TAT  GTA  GGC  TGC  GAT  ATT  CAA  AGC  TCC         445
Phe  Glu  Leu  Ser  Gly  Ile  Pro  Tyr  Val  Gly  Cys  Asp  Ile  Gln  Ser  Ser
                    115                      120                      125

GCA  GCT  TGC  ATG  GAC  AAA  TCA  CTG  GCC  TAC  ATT  CTT  ACA  AAA  AAT  GCG         493
Ala  Ala  Cys  Met  Asp  Lys  Ser  Leu  Ala  Tyr  Ile  Leu  Thr  Lys  Asn  Ala
                    130                      135                      140

GGC  ATC  GCC  GTC  CCC  GAA  TTT  CAA  ATG  ATT  GAA  AAA  GGT  GAC  AAA  CCG         541
Gly  Ile  Ala  Val  Pro  Glu  Phe  Gln  Met  Ile  Glu  Lys  Gly  Asp  Lys  Pro
              145                      150                      155

GAG  GCG  AGG  ACG  CTT  ACC  TAC  CCT  GTC  TTT  GTG  AAG  CCG  GCA  CGG  TCA         589
Glu  Ala  Arg  Thr  Leu  Thr  Tyr  Pro  Val  Phe  Val  Lys  Pro  Ala  Arg  Ser
160                      165                      170

GGT  TCG  TCC  TTT  GGC  GTA  ACC  AAA  GTA  AAC  AGT  ACG  GAA  GAA  CTA  AAC         637
Gly  Ser  Ser  Phe  Gly  Val  Thr  Lys  Val  Asn  Ser  Thr  Glu  Glu  Leu  Asn
175                      180                      185                      190

GCT  GCG  ATA  GAA  GCA  GCA  GGA  CAA  TAT  GAT  GGA  AAA  ATC  TTA  ATT  GAG         685
Ala  Ala  Ile  Glu  Ala  Ala  Gly  Gln  Tyr  Asp  Gly  Lys  Ile  Leu  Ile  Glu
                    195                      200                      205

CAA  GCG  ATT  TCG  GGC  TGT  GAG  GTC  GGC  TGC  GCG  GTC  ATG  GGA  AAC  GAG         733
Gln  Ala  Ile  Ser  Gly  Cys  Glu  Val  Gly  Cys  Ala  Val  Met  Gly  Asn  Glu
                    210                      215                      220

GAT  GAT  TTG  ATT  GTC  GGC  GAA  GTG  GAT  CAA  ATC  CGG  TTG  AGC  CAC  GGT         781
Asp  Asp  Leu  Ile  Val  Gly  Glu  Val  Asp  Gln  Ile  Arg  Leu  Ser  His  Gly
               225                      230                      235

ATC  TTC  CGC  ATC  CAT  CAG  GAA  AAC  GAG  CCG  GAA  AAA  GGC  TCA  GAG  AAT         829
Ile  Phe  Arg  Ile  His  Gln  Glu  Asn  Glu  Pro  Glu  Lys  Gly  Ser  Glu  Asn
          240                      245                      250

GCG  ATG  ATT  ATC  GTT  CCA  GCA  GAC  ATT  CCG  GTC  GAG  GAA  CGA  AAT  CGG         877
Ala  Met  Ile  Ile  Val  Pro  Ala  Asp  Ile  Pro  Val  Glu  Glu  Arg  Asn  Arg
255                      260                      265                      270

GTG  CAA  GAA  ACG  GCA  AAG  AAA  GTA  TAT  CGG  GTG  CTT  GGA  TGC  AGA  GGG         925
Val  Gln  Glu  Thr  Ala  Lys  Lys  Val  Tyr  Arg  Val  Leu  Gly  Cys  Arg  Gly
                    275                      280                      285

CTT  GCT  CGT  GTT  GAT  CTT  TTT  TTG  CAG  GAG  GAT  GGC  GGC  ATC  GTT  CTA         973
Leu  Ala  Arg  Val  Asp  Leu  Phe  Leu  Gln  Glu  Asp  Gly  Gly  Ile  Val  Leu
               290                      295                      300

AAC  GAG  GTC  AAT  ACC  CTG  CCC  GGT  TTT  ACA  TCG  TAC  AGC  CGC  TAT  CCA        1021
Asn  Glu  Val  Asn  Thr  Leu  Pro  Gly  Phe  Thr  Ser  Tyr  Ser  Arg  Tyr  Pro
          305                      310                      315

CGC  ATG  GCG  GCT  GCC  GCA  GGA  ATC  ACG  CTT  CCC  GCA  CTA  ATT  GAC  AGC        1069
Arg  Met  Ala  Ala  Ala  Ala  Gly  Ile  Thr  Leu  Pro  Ala  Leu  Ile  Asp  Ser
320                      325                      330

CTG  ATT  ACA  TTG  GCG  ATA  GAG  AGG  TGACCCGTAT  GGAAAATGGT  TTTTGTTTT          1123
Leu  Ile  Thr  Leu  Ala  Ile  Glu  Arg
335                      340

TTAGATGAAA  TGTTGCA                                                                   1140
```

(2) INFORMATION FOR SEQ ID NO:2:

(i) SEQUENCE CHARACTERISTICS:
        (A) LENGTH: 342 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asn Lys Ile Lys Val Ala Ile Ile Phe Gly Gly Cys Ser Glu Glu
 1               5                  10                  15

His Asp Val Ser Val Lys Ser Ala Ile Glu Ile Ala Ala Asn Ile Asn
                20                  25                  30

Thr Glu Lys Phe Asp Pro His Tyr Ile Gly Ile Thr Lys Asn Gly Val
            35                  40                  45

Trp Lys Leu Cys Lys Lys Pro Cys Thr Glu Trp Glu Ala Asp Ser Leu
50                      55                  60

Pro Ala Ile Phe Ser Pro Asp Arg Lys Thr His Gly Leu Leu Val Met
65                  70                      75                  80

Lys Glu Arg Glu Tyr Glu Thr Arg Arg Ile Asp Val Ala Phe Pro Val
                85                  90                  95

Leu His Gly Lys Cys Gly Glu Asp Gly Ala Ile Gln Gly Leu Phe Glu
                100                 105                 110

Leu Ser Gly Ile Pro Tyr Val Gly Cys Asp Ile Gln Ser Ser Ala Ala
            115                 120                 125

Cys Met Asp Lys Ser Leu Ala Tyr Ile Leu Thr Lys Asn Ala Gly Ile
130                     135                 140

Ala Val Pro Glu Phe Gln Met Ile Glu Lys Gly Asp Lys Pro Glu Ala
145                 150                 155                 160

Arg Thr Leu Thr Tyr Pro Val Phe Val Lys Pro Ala Arg Ser Gly Ser
                165                 170                 175

Ser Phe Gly Val Thr Lys Val Asn Ser Thr Glu Glu Leu Asn Ala Ala
            180                 185                 190

Ile Glu Ala Ala Gly Gln Tyr Asp Gly Lys Ile Leu Ile Glu Gln Ala
                195                 200                 205

Ile Ser Gly Cys Glu Val Gly Cys Ala Val Met Gly Asn Glu Asp Asp
    210                 215                 220

Leu Ile Val Gly Glu Val Asp Gln Ile Arg Leu Ser His Gly Ile Phe
225                 230                 235                 240

Arg Ile His Gln Glu Asn Glu Pro Glu Lys Gly Ser Glu Asn Ala Met
                245                 250                 255

Ile Ile Val Pro Ala Asp Ile Pro Val Glu Glu Arg Asn Arg Val Gln
            260                 265                 270

Glu Thr Ala Lys Lys Val Tyr Arg Val Leu Gly Cys Arg Gly Leu Ala
            275                 280                 285

Arg Val Asp Leu Phe Leu Gln Glu Asp Gly Gly Ile Val Leu Asn Glu
            290                 295                 300

Val Asn Thr Leu Pro Gly Phe Thr Ser Tyr Ser Arg Tyr Pro Arg Met
305                 310                 315                 320

Ala Ala Ala Ala Gly Ile Thr Leu Pro Ala Leu Ile Asp Ser Leu Ile
                325                 330                 335

Thr Leu Ala Ile Glu Arg
                340
```

(2) INFORMATION FOR SEQ ID NO:3:

( i ) SEQUENCE CHARACTERISTICS:
    ( A ) LENGTH: 589 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:3:

```
TCTGTTTGAA  TTGTCTGGTA  TCCCCTATGT  AGGCTGCGAT  ATTCAAAGCT  CCGCAGCTTG    60
CATGGACAAA  TCACTGGCCT  ACATTCTTAC  AAAAAATGCG  GGCATCGCCG  TCCCCGAATT   120
TCAAATGATT  GAAAAGGTG   ACAAACCGGA  GGCGAGGACG  CTTACCTACC  CTGTCTTTGT   180
GAAGCCGGCA  CGGTCAGGTT  CGTCCTTTGG  CGTAACCAAA  GTAAACAGTA  CGGAAGAACT   240
AAACGCTGCG  ATAGAAGCAG  CAGGACAATA  TGATGGAAAA  ATCTTAATTG  AGCAAGCGAT   300
TTCGGGCTGT  GAGGTCGGCT  GCGCGGTCAT  GGGAAACGAG  GATGATTTGA  TTGTCGGCGA   360
AGTGGATCAA  ATCCGGTTGA  GCCACGGTAT  CTTCCGCATC  CATCAGGAAA  ACGAGCCGGA   420
AAAAGGCTCA  GAGAATGCGA  TGATTATCGT  TCCAGCAGAC  ATTCCGGTCG  AGGAACGAAA   480
TCGGGTGCAA  GAAACGGCAA  AGAAAGTATA  TCGGGTGCTT  GGATGCAGAG  GGCTTGCTCG   540
TGTTGATCTT  TTTTTGCAGG  AGGATGGCGG  CATCGTTCTA  AACGAGGTC                589
```

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:4:

```
ATGGGAAGCC  GATAGTC                                                       17
```

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:5:

```
GATTTCGTTC  CTCGACC                                                       17
```

( 2 ) INFORMATION FOR SEQ ID NO:6:

( i ) SEQUENCE CHARACTERISTICS:
        ( A ) LENGTH: 343 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:6:

```
Met  Asn  Arg  Ile  Lys  Val  Ala  Ile  Leu  Phe  Gly  Gly  Cys  Ser  Glu  Glu
  1                5                         10                        15

His  Asp  Val  Ser  Val  Lys  Ser  Ala  Ile  Glu  Ile  Ala  Ala  Asn  Ile  Asn
                  20                         25                        30

Lys  Glu  Lys  Tyr  Glu  Pro  Leu  Tyr  Ile  Gly  Ile  Thr  Lys  Ser  Gly  Val
```

|   | 23 | | | | | | | | | | | | 24 | |
|---|---|---|---|---|---|---|---|---|---|---|---|---|---|---|

-continued

```
                        35                          40                          45
        Trp  Lys  Met  Cys  Glu  Lys  Pro  Cys  Ala  Glu  Trp  Glu  Asn  Asp  Asn  Cys
             50                       55                       60

Tyr  Ser  Ala  Val  Leu  Ser  Pro  Asp  Lys  Lys  Met  His  Gly  Leu  Leu  Val
        65                       70                       75                            80

Lys  Lys  Asn  His  Glu  Tyr  Glu  Ile  Asn  His  Val  Asp  Val  Ala  Phe  Ser
                       85                       90                            95

Ala  Leu  His  Gly  Lys  Ser  Gly  Glu  Asp  Gly  Ser  Ile  Gln  Gly  Leu  Phe
                       100                      105                      110

Glu  Leu  Ser  Gly  Ile  Pro  Phe  Val  Gly  Cys  Asp  Ile  Gln  Ser  Ser  Ala
                       115                      120                      125

Ile  Cys  Met  Asp  Lys  Ser  Leu  Thr  Tyr  Ile  Val  Ala  Lys  Asn  Ala  Gly
             130                      135                      140

Ile  Ala  Thr  Pro  Ala  Phe  Trp  Val  Ile  Asn  Lys  Asp  Asp  Arg  Pro  Val
        145                      150                      155                           160

Ala  Ala  Thr  Phe  Thr  Tyr  Pro  Val  Phe  Val  Lys  Pro  Ala  Arg  Ser  Gly
                            165                      170                      175

Ser  Ser  Phe  Gly  Val  Lys  Lys  Val  Asn  Ser  Ala  Asp  Glu  Leu  Asp  Tyr
                       180                      185                      190

Ala  Ile  Glu  Ser  Ala  Arg  Gln  Tyr  Asp  Ser  Lys  Ile  Leu  Ile  Glu  Gln
                       195                      200                      205

Ala  Val  Ser  Gly  Cys  Glu  Val  Gly  Cys  Ala  Val  Leu  Gly  Asn  Ser  Ala
             210                      215                      220

Ala  Leu  Val  Val  Gly  Glu  Val  Asp  Gln  Ile  Arg  Leu  Gln  Tyr  Gly  Ile
        225                      230                      235                           240

Phe  Arg  Ile  His  Gln  Glu  Val  Glu  Pro  Glu  Lys  Gly  Ser  Glu  Asn  Ala
                            245                      250                      255

Val  Ile  Thr  Val  Pro  Ala  Asp  Leu  Ser  Ala  Glu  Glu  Arg  Gly  Arg  Ile
                       260                      265                      270

Gln  Glu  Thr  Ala  Lys  Lys  Ile  Tyr  Lys  Ala  Leu  Gly  Cys  Arg  Gly  Leu
                       275                      280                      285

Ala  Arg  Val  Asp  Met  Phe  Leu  Gln  Asp  Asn  Gly  Arg  Ile  Val  Leu  Asn
             290                      295                      300

Glu  Val  Asn  Thr  Leu  Pro  Gly  Phe  Thr  Ser  Tyr  Ser  Arg  Tyr  Pro  Arg
        305                      310                      315                           320

Met  Met  Ala  Ala  Ala  Gly  Ile  Ala  Leu  Pro  Glu  Leu  Ile  Asp  Arg  Leu
                            325                      330                      335

Ile  Val  Leu  Ala  Leu  Lys  Gly
                            340
```

( 2 ) INFORMATION FOR SEQ ID NO:7:

( i ) SEQUENCE CHARACTERISTICS:
        ( A ) LENGTH: 343 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:7:

```
        Met  Lys  Lys  Ile  Ala  Val  Leu  Phe  Gly  Gly  Asn  Ser  Pro  Glu  Tyr  Ser
        1                   5                        10                           15

Val  Ser  Leu  Thr  Ser  Ala  Ala  Ser  Val  Ile  Gln  Ala  Ile  Asp  Pro  Leu
                       20                       25                       30

Lys  Tyr  Glu  Val  Met  Thr  Ile  Gly  Ile  Ala  Pro  Thr  Met  Asp  Trp  Tyr
                       35                       40                       45
```

```
Trp Tyr Gln Gly Asn Leu Ala Asn Val Arg Asn Asp Thr Trp Leu Glu
    50                  55                  60

Asp His Lys Asn Cys His Gln Leu Thr Phe Ser Ser Gln Gly Phe Ile
65              70                  75                      80

Leu Gly Glu Lys Arg Ile Val Pro Asp Val Leu Phe Pro Val Leu His
                85                  90                      95

Gly Lys Tyr Gly Glu Asp Gly Cys Ile Gln Gly Leu Leu Glu Leu Met
            100             105             110

Asn Leu Pro Tyr Val Gly Cys His Val Ala Ala Ser Ala Leu Cys Met
            115             120             125

Asn Lys Trp Leu Leu His Gln Leu Ala Asp Thr Met Gly Ile Ala Ser
    130             135             140

Ala Pro Thr Leu Leu Leu Ser Arg Tyr Glu Asn Asp Pro Ala Thr Ile
145             150             155                     160

Asp Arg Phe Ile Gln Asp His Gly Phe Pro Ile Phe Ile Lys Pro Asn
                165             170             175

Glu Ala Gly Ser Ser Lys Gly Ile Thr Lys Val Thr Asp Lys Thr Ala
            180             185             190

Leu Gln Ser Ala Leu Thr Thr Ala Phe Ala Tyr Gly Ser Thr Val Leu
        195             200             205

Ile Gln Lys Ala Ile Ala Gly Ile Glu Ile Gly Cys Gly Ile Leu Gly
    210             215             220

Asn Glu Gln Leu Thr Ile Gly Ala Cys Asp Ala Ile Ser Leu Val Asp
225             230             235                     240

Gly Phe Phe Asp Phe Glu Glu Lys Tyr Gln Leu Ile Ser Ala Thr Ile
            245             250             255

Thr Val Pro Ala Pro Leu Pro Leu Ala Leu Glu Ser Gln Ile Lys Glu
            260             265             270

Gln Ala Gln Leu Leu Tyr Arg Asn Leu Gly Leu Thr Gly Leu Ala Arg
        275             280             285

Ile Asp Phe Phe Val Thr Asn Gln Gly Ala Ile Tyr Leu Asn Glu Ile
    290             295             300

Asn Thr Met Pro Gly Phe Thr Gly His Ser Arg Tyr Pro Ala Met Met
305             310             315                     320

Ala Glu Val Gly Leu Ser Tyr Glu Ile Leu Val Glu Gln Leu Ile Ala
            325             330             335

Leu Ala Glu Glu Asp Lys Arg
            340
```

( 2 ) INFORMATION FOR SEQ ID NO:8:

( i ) SEQUENCE CHARACTERISTICS:
        ( A ) LENGTH: 348 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:8:

```
Leu Lys Ile Ile Leu Leu Tyr Gly Gly Arg Ser Glu Glu His Asp Val
1               5                   10                  15

Ser Val Leu Ser Ala Tyr Ser Val Leu Asn Ala Ile Tyr Tyr Lys Tyr
            20                  25                  30

Tyr Gln Val Gln Leu Val Phe Ile Ser Lys Asp Gly Gln Trp Val Lys
        35                  40                  45
```

| Gly | Pro | Leu | Leu | Ser | Glu | Arg | Pro | Gln | Asn | Lys | Glu | Val | Leu | His | Leu |
| --- | --- | --- | --- | --- | --- | --- | --- | --- | --- | --- | --- | --- | --- | --- | --- |
| | 50 | | | | 55 | | | | | 60 | | | | | |
| Thr | Trp | Ala | Gln | Thr | Pro | Glu | Glu | Thr | Gly | Glu | Phe | Ser | Gly | Lys | Arg |
| 65 | | | | | 70 | | | | | 75 | | | | | 80 |
| Ile | Ser | Pro | Ser | Glu | Ile | Tyr | Glu | Glu | Ala | Ile | Val | Phe | Pro | Val | |
| | | | | 85 | | | | | 90 | | | | | 95 | |
| Leu | His | Gly | Pro | Asn | Gly | Glu | Asp | Gly | Ser | Ile | Gln | Gly | Phe | Met | Glu |
| | | | 100 | | | | | 105 | | | | | 110 | | |
| Thr | Ile | Asn | Met | Pro | Tyr | Val | Gly | Ala | Gly | Val | Leu | Ala | Ser | Ala | Asn |
| | | 115 | | | | 120 | | | | | 125 | | | | |
| Ala | Met | Asp | Lys | Ile | Met | Thr | Lys | Val | Leu | Leu | Gln | Thr | Val | Gly | Ile |
| | 130 | | | | 135 | | | | | 140 | | | | | |
| Pro | Gln | Val | Pro | Phe | Val | Pro | Val | Leu | Arg | Ser | Asp | Trp | Lys | Gly | Asn |
| 145 | | | | | 150 | | | | | 155 | | | | | 160 |
| Pro | Lys | Glu | Val | Thr | Glu | Lys | Cys | Glu | Gly | Ser | Leu | Ile | Tyr | Pro | Val |
| | | | | 165 | | | | | 170 | | | | | 175 | |
| Phe | Val | Lys | Pro | Ala | Asn | Met | Gly | Ser | Ser | Val | Gly | Ile | Ser | Lys | Val |
| | | | 180 | | | | | 185 | | | | | 190 | | |
| Glu | Asn | Arg | Asp | Glu | Leu | Gln | Glu | Ala | Leu | Glu | Glu | Ala | Phe | Arg | Tyr |
| | | 195 | | | | 200 | | | | | 205 | | | | |
| Asp | Ala | Arg | Ala | Ile | Val | Glu | Gln | Gly | Ile | Glu | Ala | Arg | Glu | Ile | Glu |
| | 210 | | | | 215 | | | | | 220 | | | | | |
| Val | Ala | Ile | Leu | Gly | Asn | Glu | Asp | Val | Arg | Thr | Thr | Leu | Pro | Gly | Glu |
| 225 | | | | | 230 | | | | | 235 | | | | | 240 |
| Val | Val | Lys | Asp | Val | Ala | Phe | Tyr | Asp | Tyr | Asp | Ala | Lys | Tyr | Ile | Asn |
| | | | | 245 | | | | | 250 | | | | | 255 | |
| Asn | Thr | Ile | Glu | Met | Gln | Ile | Pro | Ala | His | Val | Pro | Glu | Glu | Val | Ala |
| | | | 260 | | | | | 265 | | | | | 270 | | |
| His | Gln | Ala | Gln | Glu | Tyr | Ala | Lys | Lys | Ala | Tyr | Ile | Met | Leu | Asp | Gly |
| | | 275 | | | | 280 | | | | | 285 | | | | |
| Ser | Gly | Leu | Ser | Arg | Cys | Asp | Phe | Phe | Leu | Thr | Ser | Lys | Asn | Glu | Leu |
| | 290 | | | | 295 | | | | | 300 | | | | | |
| Phe | Leu | Asn | Glu | Leu | Asn | Thr | Met | Pro | Gly | Phe | Thr | Pro | Phe | Ser | Met |
| 305 | | | | | 310 | | | | | 315 | | | | | 320 |
| Tyr | Pro | Leu | Leu | Trp | Glu | Asn | Met | Gly | Leu | Lys | Tyr | Ser | Asp | Leu | Ile |
| | | | | 325 | | | | | 330 | | | | | 335 | |
| Glu | Glu | Leu | Ile | Gln | Leu | Ala | Leu | Asn | Arg | Phe | Lys | | | | |
| | | | 340 | | | | | 345 | | | | | | | |

( 2 ) INFORMATION FOR SEQ ID NO:9:

( i ) SEQUENCE CHARACTERISTICS:
    ( A ) LENGTH: 364 amino acids
    ( B ) TYPE: amino acid
    ( C ) STRANDEDNESS: Not Relevant
    ( D ) TOPOLOGY: linear ( i i ) MOLECULE TYPE: protein ( x i ) SEQUENCE DESCRIPTION: SEQ ID NO:9:

| Met | Glu | Lys | Leu | Arg | Val | Gly | Ile | Val | Phe | Gly | Gly | Lys | Ser | Ala | Glu |
| --- | --- | --- | --- | --- | --- | --- | --- | --- | --- | --- | --- | --- | --- | --- | --- |
| 1 | | | | 5 | | | | | 10 | | | | | 15 | |
| His | Glu | Val | Ser | Leu | Gln | Ser | Ala | Lys | Asn | Ile | Val | Asp | Ala | Ile | Asp |
| | | | 20 | | | | | 25 | | | | | 30 | | |
| Lys | Ser | Arg | Phe | Asp | Val | Val | Leu | Leu | Gly | Ile | Asp | Lys | Gln | Gly | Gln |
| | | 35 | | | | | 40 | | | | | 45 | | | |
| Trp | His | Val | Ser | Asp | Ala | Ser | Asn | Tyr | Leu | Leu | Asn | Ala | Asp | Asp | Pro |

|                |                |                |                |                |                |                |                |                |                |                |                |                |                |                |                |
|---|---|---|---|---|---|---|---|---|---|---|---|---|---|---|---|

|     |     |     | 50  |     |     |     | 55  |     |     |     | 60  |     |     |     |     |
|-----|-----|-----|-----|-----|-----|-----|-----|-----|-----|-----|-----|-----|-----|-----|-----|
| Ala | His | Ile | Ala | Leu | Arg | Pro | Ser | Ala | Thr | Ser | Leu | Ala | Gln | Val | Pro |
| 65  |     |     |     |     | 70  |     |     |     | 75  |     |     |     |     |     | 80  |
| Gly | Lys | His | Glu | His | Gln | Leu | Ile | Asp | Ala | Gln | Asn | Gly | Gln | Pro | Leu |
|     |     |     |     | 85  |     |     |     |     | 90  |     |     |     |     | 95  |     |
| Pro | Thr | Val | Asp | Val | Ile | Phe | Pro | Ile | Val | His | Gly | Thr | Leu | Gly | Glu |
|     |     |     | 100 |     |     |     |     | 105 |     |     |     |     | 110 |     |     |
| Asp | Gly | Ser | Leu | Gln | Gly | Met | Leu | Arg | Val | Ala | Asn | Leu | Pro | Phe | Val |
|     |     |     | 115 |     |     |     | 120 |     |     |     |     | 125 |     |     |     |
| Gly | Ser | Asp | Val | Leu | Ala | Ser | Ala | Ala | Cys | Met | Asp | Lys | Asp | Val | Thr |
|     |     | 130 |     |     |     | 135 |     |     |     |     | 140 |     |     |     |     |
| Lys | Arg | Leu | Leu | Arg | Asp | Ala | Gly | Leu | Asn | Ile | Ala | Pro | Phe | Ile | Thr |
| 145 |     |     |     |     | 150 |     |     |     | 155 |     |     |     |     |     | 160 |
| Leu | Thr | Arg | Ala | Asn | Arg | His | Asn | Ile | Ser | Phe | Ala | Glu | Val | Glu | Ser |
|     |     |     |     | 165 |     |     |     |     | 170 |     |     |     |     | 175 |     |
| Lys | Leu | Gly | Leu | Pro | Leu | Phe | Val | Lys | Pro | Ala | Asn | Gln | Gly | Ser | Ser |
|     |     |     | 180 |     |     |     |     | 185 |     |     |     |     | 190 |     |     |
| Val | Gly | Val | Ser | Lys | Val | Thr | Ser | Glu | Glu | Gln | Tyr | Ala | Ile | Ala | Val |
|     |     | 195 |     |     |     |     | 200 |     |     |     |     | 205 |     |     |     |
| Asp | Leu | Ala | Phe | Glu | Phe | Asp | His | Lys | Val | Ile | Val | Glu | Gln | Gly | Ile |
|     | 210 |     |     |     |     | 215 |     |     |     |     | 220 |     |     |     |     |
| Lys | Gly | Arg | Glu | Ile | Glu | Cys | Ala | Val | Leu | Gly | Asn | Asp | Asn | Pro | Gln |
| 225 |     |     |     |     | 230 |     |     |     |     | 235 |     |     |     |     | 240 |
| Ala | Ser | Thr | Cys | Gly | Glu | Ile | Val | Leu | Thr | Ser | Asp | Phe | Tyr | Ala | Tyr |
|     |     |     |     | 245 |     |     |     |     | 250 |     |     |     |     | 255 |     |
| Asp | Thr | Lys | Tyr | Ile | Asp | Glu | Asp | Gly | Ala | Lys | Val | Val | Val | Pro | Ala |
|     |     |     | 260 |     |     |     |     | 265 |     |     |     |     | 270 |     |     |
| Ala | Ile | Ala | Pro | Glu | Ile | Asn | Asp | Lys | Ile | Arg | Ala | Ile | Ala | Val | Gln |
|     |     | 275 |     |     |     |     | 280 |     |     |     |     | 285 |     |     |     |
| Ala | Tyr | Gln | Thr | Leu | Gly | Cys | Ala | Gly | Met | Ala | Arg | Val | Asp | Val | Phe |
|     | 290 |     |     |     |     | 295 |     |     |     |     | 300 |     |     |     |     |
| Leu | Thr | Pro | Glu | Asn | Glu | Val | Val | Ile | Asn | Glu | Ile | Asn | Thr | Leu | Pro |
| 305 |     |     |     |     | 310 |     |     |     |     | 315 |     |     |     |     | 320 |
| Gly | Phe | Thr | Asn | Ile | Ser | Met | Tyr | Pro | Lys | Leu | Trp | Gln | Ala | Ser | Gly |
|     |     |     |     | 325 |     |     |     |     | 330 |     |     |     |     | 335 |     |
| Leu | Gly | Tyr | Thr | Asp | Leu | Ile | Thr | Arg | Leu | Ile | Glu | Leu | Ala | Leu | Glu |
|     |     |     | 340 |     |     |     |     | 345 |     |     |     |     | 350 |     |     |
| Arg | His | Ala | Ala | Asn | Asn | Ala | Leu | Lys | Thr | Thr | Met |     |     |     |     |
|     |     | 355 |     |     |     |     | 360 |     |     |     |     |     |     |     |     |

( 2 ) INFORMATION FOR SEQ ID NO:10:

( i ) SEQUENCE CHARACTERISTICS:
        ( A ) LENGTH: 364 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:10:

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Ala | Lys | Leu | Arg | Val | Gly | Ile | Val | Phe | Gly | Gly | Lys | Ser | Ala | Glu |
| 1   |     |     |     | 5   |     |     |     |     | 10  |     |     |     |     | 15  |     |
| His | Glu | Val | Ser | Leu | Gln | Ser | Ala | Lys | Asn | Ile | Val | Asp | Ala | Ile | Asp |
|     |     |     | 20  |     |     |     |     | 25  |     |     |     |     | 30  |     |     |
| Lys | Thr | Arg | Phe | Asp | Val | Val | Leu | Leu | Gly | Ile | Asp | Lys | Ala | Gly | Gln |
|     |     | 35  |     |     |     |     | 40  |     |     |     |     | 45  |     |     |     |

```
Trp His Val Asn Asp Ala Glu Asn Tyr Leu Gln Asn Ala Asp Asp Pro
    50                  55                  60
Ala His Ile Ala Leu Arg Pro Ser Ala Ile Ser Leu Ala Gln Val Pro
65                  70                  75                  80
Gly Lys His Gln His Gln Leu Ile Asn Ala Gln Asn Gly Gln Pro Leu
                85                  90                  95
Pro Thr Val Asp Val Ile Phe Pro Ile Val His Gly Thr Leu Gly Glu
                100                 105                 110
Asp Gly Ser Leu Gln Gly Met Leu Arg Val Ala Asn Leu Pro Phe Val
            115                 120                 125
Gly Ser Asp Val Leu Ser Ser Ala Ala Cys Met Asp Lys Asp Val Ala
        130                 135                 140
Lys Arg Leu Leu Arg Asp Ala Gly Leu Asn Ile Ala Pro Phe Ile Thr
145                 150                 155                 160
Leu Thr Arg Thr Asn Arg His Ala Phe Ser Phe Ala Glu Val Glu Ser
                165                 170                 175
Arg Leu Gly Leu Pro Leu Phe Val Lys Pro Ala Asn Gln Gly Ser Ser
                180                 185                 190
Val Gly Val Ser Lys Val Ala Asn Glu Ala Gln Tyr Gln Gln Ala Val
        195                 200                 205
Ala Leu Ala Phe Glu Phe Asp His Lys Val Val Val Glu Gln Gly Ile
        210                 215                 220
Lys Gly Arg Glu Ile Glu Cys Ala Val Leu Gly Asn Asp Asn Pro Gln
225                 230                 235                 240
Ala Ser Thr Cys Gly Glu Ile Val Leu Asn Ser Glu Phe Tyr Ala Tyr
                245                 250                 255
Asp Thr Lys Tyr Ile Asp Asp Asn Gly Ala Gln Val Val Val Pro Ala
            260                 265                 270
Gln Ile Pro Ser Glu Val Asn Asp Lys Ile Arg Ala Ile Ala Ile Gln
        275                 280                 285
Ala Tyr Gln Thr Leu Gly Cys Ala Gly Met Ala Arg Val Asp Val Phe
        290                 295                 300
Leu Thr Ala Asp Asn Glu Val Val Ile Asn Glu Ile Asn Thr Leu Pro
305                 310                 315                 320
Gly Phe Thr Asn Ile Ser Met Tyr Pro Lys Leu Trp Gln Ala Ser Gly
                325                 330                 335
Leu Gly Tyr Thr Asp Leu Ile Ser Arg Leu Ile Glu Leu Ala Leu Glu
            340                 345                 350
Arg His Thr Ala Asn Asn Ala Leu Lys Thr Thr Met
        355                 360
```

( 2 ) INFORMATION FOR SEQ ID NO:11:

( i ) SEQUENCE CHARACTERISTICS:
        ( A ) LENGTH: 306 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:11:

```
Met Thr Asp Lys Ile Ala Val Leu Leu Gly Gly Thr Ser Ala Glu Arg
1               5                   10                  15
Glu Val Ser Leu Asn Ser Gly Ala Ala Val Leu Ala Gly Leu Arg Glu
            20                  25                  30
```

| | | | | | | | | | | | | | | |
|---|---|---|---|---|---|---|---|---|---|---|---|---|---|---|
| Gly | Gly | Ile 35 | Asp | Ala | Tyr | Pro | Val 40 | Asp | Pro | Lys | Glu | Val 45 | Asp | Val | Thr |
| Gln | Leu 50 | Lys | Ser | Met | Gly | Phe 55 | Gln | Lys | Val | Phe | Ile 60 | Ala | Leu | His | Gly |
| Arg 65 | Gly | Gly | Glu | Asp | Gly 70 | Thr | Leu | Gln | Gly | Met 75 | Leu | Glu | Leu | Met | Gly 80 |
| Leu | Pro | Tyr | Thr | Gly 85 | Ser | Gly | Val | Met | Ala 90 | Ser | Ala | Leu | Ser | Met 95 | Asp |
| Lys | Leu | Arg | Ser 100 | Lys | Leu | Leu | Trp | Gln 105 | Gly | Ala | Gly | Leu | Pro 110 | Val | Ala |
| Pro | Trp | Val 115 | Ala | Leu | Thr | Arg | Ala 120 | Glu | Phe | Glu | Lys | Gly 125 | Leu | Ser | Asp |
| Lys | Gln 130 | Leu | Ala | Glu | Ile | Ser 135 | Ala | Leu | Gly | Leu | Pro 140 | Val | Ile | Val | Lys |
| Pro 145 | Ser | Arg | Glu | Gly | Ser 150 | Ser | Val | Gly | Met | Ser 155 | Lys | Val | Val | Ala | Glu 160 |
| Asn | Ala | Leu | Gln | Asp 165 | Ala | Leu | Arg | Leu | Ala 170 | Phe | Gln | His | Asp | Glu 175 | Glu |
| Val | Leu | Ile | Glu 180 | Lys | Trp | Leu | Ser | Gly 185 | Pro | Glu | Phe | Thr | Val 190 | Ala | Ile |
| Leu | Gly | Glu 195 | Glu | Ile | Leu | Pro | Ser 200 | Ile | Arg | Ile | Gln | Pro 205 | Ser | Gly | Thr |
| Phe | Tyr 210 | Asp | Tyr | Glu | Ala | Lys 215 | Tyr | Leu | Ser | Asp | Glu 220 | Thr | Gln | Tyr | Phe |
| Cys 225 | Pro | Ala | Gly | Leu | Glu 230 | Ala | Ser | Gln | Glu | Ala 235 | Asn | Leu | Gln | Ala | Leu 240 |
| Val | Leu | Lys | Ala | Trp 245 | Thr | Thr | Leu | Gly | Cys 250 | Lys | Gly | Trp | Gly | Arg 255 | Ile |
| Asp | Val | Met | Leu 260 | Asp | Ser | Asp | Gly | Gln 265 | Phe | Tyr | Leu | Leu | Glu 270 | Ala | Asn |
| Thr | Ser | Pro 275 | Gly | Met | Thr | Ser | His 280 | Ser | Leu | Val | Pro | Met 285 | Ala | Ala | Arg |
| Gln | Ala 290 | Gly | Met | Ser | Phe | Ser 295 | Gln | Leu | Val | Val | Arg 300 | Ile | Leu | Glu | Leu |
| Ala 305 | Asp | | | | | | | | | | | | | | |

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:12:

GGNGARGAYG GNWSNYTNCA RGGN    24

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:13:

AAYACNHTNC CNGGNTTTAC N                                                                                        21

( 2 ) INFORMATION FOR SEQ ID NO:14:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:14:

GGNGARGAYG GNRSNHTNCA RGG                                                                                      23

( 2 ) INFORMATION FOR SEQ ID NO:15:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:15:

TGRAANCCNG GNADNGTRTT                                                                                          20

( 2 ) INFORMATION FOR SEQ ID NO:16:

( i ) SEQUENCE CHARACTERISTICS:
    ( A ) LENGTH: 1079 base pairs
    ( B ) TYPE: nucleic acid
    ( C ) STRANDEDNESS: double
    ( D ) TOPOLOGY: linear ( i i ) MOLECULE TYPE: DNA (genomic)

( i x ) FEATURE:
    ( A ) NAME/KEY: CDS
    ( B ) LOCATION: 33..1076

( x i ) SEQUENCE DESCRIPTION: SEQ ID NO:16:

```
AAAGACAGGA AAGAAACTAG GAGGACAAGC AT TTG AAG ATT ATT TTG TTG TAT       53
                                   Leu Lys Ile Ile Leu Leu Tyr
                                            345

GGC GGC AGA AGT GAA GAG CAC GAT GTG TCT GTT TTG TCT GCA TAT TCC      101
Gly Gly Arg Ser Glu Glu His Asp Val Ser Val Leu Ser Ala Tyr Ser
350                     355                 360                 365

GTT TTA AAT GCA ATC TAT TAT AAA TAT TAT CAA GTA CAG TTA GTC TTT      149
Val Leu Asn Ala Ile Tyr Tyr Lys Tyr Tyr Gln Val Gln Leu Val Phe
                370                 375                 380

ATT AGT AAA GAC GGT CAA TGG GTA AAA GGC CCT CTT TTA TCT GAA CGA      197
Ile Ser Lys Asp Gly Gln Trp Val Lys Gly Pro Leu Leu Ser Glu Arg
            385                 390                 395

CCA CAA AAT AAA GAA GTT TTA CAT TTA ACT TGG GCA CAA ACA CCT GAA      245
Pro Gln Asn Lys Glu Val Leu His Leu Thr Trp Ala Gln Thr Pro Glu
        400                 405                 410

GAA ACA GGC GAA TTT TCA GGA AAA CGA ATC AGT CCT TCG GAA ATT TAT      293
Glu Thr Gly Glu Phe Ser Gly Lys Arg Ile Ser Pro Ser Glu Ile Tyr
    415                 420                 425

GAA GAA GAA GCG ATT GTT TTC CCT GTT TTA CAT GGG CCA AAT GGT GAA      341
Glu Glu Glu Ala Ile Val Phe Pro Val Leu His Gly Pro Asn Gly Glu
430                 435                 440                 445

GAT GGA ACA ATT CAA GGA TTC ATG GAA ACC ATT AAT ATG CCT TAT GTA      389
```

-continued

| | | | | | | | | | | | | | | | | |
|---|---|---|---|---|---|---|---|---|---|---|---|---|---|---|---|---|
| Asp | Gly | Thr | Ile | Gln | Gly | Phe | Met | Glu | Thr | Ile | Asn | Met | Pro | Tyr | Val | |
| | | | | 450 | | | | 455 | | | | | | 460 | | |
| GGC | GCG | GGT | GTC | TTA | GCT | AGC | GTT | AAC | GCA | ATG | GAC | AAA | ATC | ATG | ACG | 437 |
| Gly | Ala | Gly | Val | Leu | Ala | Ser | Val | Asn | Ala | Met | Asp | Lys | Ile | Met | Thr | |
| | | | 465 | | | | | 470 | | | | | 475 | | | |
| AAA | TAT | CTT | TTA | CAA | ACT | GTT | GGC | ATT | CCA | CAA | GTA | CCA | TTC | GTG | CCA | 485 |
| Lys | Tyr | Leu | Leu | Gln | Thr | Val | Gly | Ile | Pro | Gln | Val | Pro | Phe | Val | Pro | |
| | | | 480 | | | | 485 | | | | | 490 | | | | |
| GTT | TTA | AGA | AGT | GAC | TGG | AAA | GGA | AAT | CCA | AAA | GAA | GTC | TTT | GAA | AAA | 533 |
| Val | Leu | Arg | Ser | Asp | Trp | Lys | Gly | Asn | Pro | Lys | Glu | Val | Phe | Glu | Lys | |
| | 495 | | | | 500 | | | | | | 505 | | | | | |
| TGT | GAA | GGT | TCT | TTA | ATT | TAT | CCG | GTC | TTT | GTT | AAA | CCT | GCC | AAT | ATG | 581 |
| Cys | Glu | Gly | Ser | Leu | Ile | Tyr | Pro | Val | Phe | Val | Lys | Pro | Ala | Asn | Met | |
| 510 | | | | | 515 | | | | | 520 | | | | | 525 | |
| GGT | TCT | AGT | GTC | GGA | ATT | AGC | AAA | GTG | GAA | AAT | CGT | GAA | GAA | TTG | CAA | 629 |
| Gly | Ser | Ser | Val | Gly | Ile | Ser | Lys | Val | Glu | Asn | Arg | Glu | Glu | Leu | Gln | |
| | | | | 530 | | | | | 535 | | | | | 540 | | |
| GAA | GCA | TTG | GAA | GAA | GCT | TTC | CGT | TAT | GAT | GCC | CGA | GCA | ATT | GTT | GAA | 677 |
| Glu | Ala | Leu | Glu | Glu | Ala | Phe | Arg | Tyr | Asp | Ala | Arg | Ala | Ile | Val | Glu | |
| | | 545 | | | | | 550 | | | | | 555 | | | | |
| CAA | GGG | ATC | GAA | GCA | CGT | GAA | ATT | GAA | GTA | GCC | ATT | TTA | GGA | AAT | GAA | 725 |
| Gln | Gly | Ile | Glu | Ala | Arg | Glu | Ile | Glu | Val | Ala | Ile | Leu | Gly | Asn | Glu | |
| | | 560 | | | | | 565 | | | | | 570 | | | | |
| GAT | GTC | CGT | ACG | ACT | TTA | CCT | GGT | GAA | GTG | GTG | AAA | GAT | GTC | GCT | TTC | 773 |
| Asp | Val | Arg | Thr | Thr | Leu | Pro | Gly | Glu | Val | Val | Lys | Asp | Val | Ala | Phe | |
| | 575 | | | | | 580 | | | | | 585 | | | | | |
| TAT | GAT | TAT | GAT | GCA | AAA | TAC | ATC | AAT | AAC | ACG | ATT | GAA | ATG | CAA | ATC | 821 |
| Tyr | Asp | Tyr | Asp | Ala | Lys | Tyr | Ile | Asn | Asn | Thr | Ile | Glu | Met | Gln | Ile | |
| 590 | | | | | 595 | | | | | 600 | | | | | 605 | |
| CCA | GCG | CAT | GTT | CCA | GAA | GAA | GTA | GCT | CAT | CAA | GCG | CAA | GAA | TAC | GCT | 869 |
| Pro | Ala | His | Val | Pro | Glu | Glu | Val | Ala | His | Gln | Ala | Gln | Glu | Tyr | Ala | |
| | | | | 610 | | | | | 615 | | | | | 620 | | |
| AAA | AAA | GCG | TAT | ATT | ATG | TTA | GAT | GGA | AGT | GGC | TTA | AGT | CGC | TGT | GAT | 917 |
| Lys | Lys | Ala | Tyr | Ile | Met | Leu | Asp | Gly | Ser | Gly | Leu | Ser | Arg | Cys | Asp | |
| | | | 625 | | | | | 630 | | | | | 635 | | | |
| TTC | TTC | TTA | ACA | AGC | AAA | AAC | GAA | TTA | TTC | CTG | AAT | GAA | TTG | AAC | ACC | 965 |
| Phe | Phe | Leu | Thr | Ser | Lys | Asn | Glu | Leu | Phe | Leu | Asn | Glu | Leu | Asn | Thr | |
| | | 640 | | | | | 645 | | | | | 650 | | | | |
| ATG | CCT | GGT | TTT | ACT | GAC | TTT | AGT | ATG | TAT | CCT | TTA | CTG | TGG | GAA | AAT | 1013 |
| Met | Pro | Gly | Phe | Thr | Asp | Phe | Ser | Met | Tyr | Pro | Leu | Leu | Trp | Glu | Asn | |
| | 655 | | | | | 660 | | | | | 665 | | | | | |
| ATG | GGC | TTG | AAA | TAC | AGT | GAT | TTA | ATT | GAG | GAA | CTG | ATT | CAG | TTA | GCT | 1061 |
| Met | Gly | Leu | Lys | Tyr | Ser | Asp | Leu | Ile | Glu | Glu | Leu | Ile | Gln | Leu | Ala | |
| 670 | | | | | 675 | | | | | 680 | | | | | 685 | |
| TTG | AAT | CGT | TTT | AAA | TAA | | | | | | | | | | | 1079 |
| Leu | Asn | Arg | Phe | Lys | | | | | | | | | | | | |
| | | | | 690 | | | | | | | | | | | | |

( 2 ) INFORMATION FOR SEQ ID NO:17:

( i ) SEQUENCE CHARACTERISTICS:
        ( A ) LENGTH: 348 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

| Leu | Lys | Ile | Ile | Leu | Leu | Tyr | Gly | Gly | Arg | Ser | Glu | Glu | His | Asp | Val |
|---|---|---|---|---|---|---|---|---|---|---|---|---|---|---|---|
| 1 | | | | 5 | | | | | 10 | | | | | 15 | |
| Ser | Val | Leu | Ser | Ala | Tyr | Ser | Val | Leu | Asn | Ala | Ile | Tyr | Tyr | Lys | Tyr |
| | | | 20 | | | | | 25 | | | | | 30 | | |

-continued

```
Tyr Gln Val Gln Leu Val Phe Ile Ser Lys Asp Gly Gln Trp Val Lys
         35                  40                  45
Gly Pro Leu Leu Ser Glu Arg Pro Gln Asn Lys Glu Val Leu His Leu
         50                  55                  60
Thr Trp Ala Gln Thr Pro Glu Glu Thr Gly Glu Phe Ser Gly Lys Arg
 65                  70                  75                  80
Ile Ser Pro Ser Glu Ile Tyr Glu Glu Glu Ala Ile Val Phe Pro Val
                 85                  90                  95
Leu His Gly Pro Asn Gly Glu Asp Gly Thr Ile Gln Gly Phe Met Glu
                100                 105                 110
Thr Ile Asn Met Pro Tyr Val Gly Ala Gly Val Leu Ala Ser Val Asn
             115                 120                 125
Ala Met Asp Lys Ile Met Thr Lys Tyr Leu Leu Gln Thr Val Gly Ile
     130                 135                 140
Pro Gln Val Pro Phe Val Pro Val Leu Arg Ser Asp Trp Lys Gly Asn
145                 150                 155                 160
Pro Lys Glu Val Phe Glu Lys Cys Glu Gly Ser Leu Ile Tyr Pro Val
                165                 170                 175
Phe Val Lys Pro Ala Asn Met Gly Ser Ser Val Gly Ile Ser Lys Val
             180                 185                 190
Glu Asn Arg Glu Glu Leu Gln Glu Ala Leu Glu Glu Ala Phe Arg Tyr
         195                 200                 205
Asp Ala Arg Ala Ile Val Glu Gln Gly Ile Glu Ala Arg Glu Ile Glu
     210                 215                 220
Val Ala Ile Leu Gly Asn Glu Asp Val Arg Thr Thr Leu Pro Gly Glu
225                 230                 235                 240
Val Val Lys Asp Val Ala Phe Tyr Asp Tyr Asp Ala Lys Tyr Ile Asn
                245                 250                 255
Asn Thr Ile Glu Met Gln Ile Pro Ala His Val Pro Glu Glu Val Ala
             260                 265                 270
His Gln Ala Gln Glu Tyr Ala Lys Lys Ala Tyr Ile Met Leu Asp Gly
         275                 280                 285
Ser Gly Leu Ser Arg Cys Asp Phe Phe Leu Thr Ser Lys Asn Glu Leu
     290                 295                 300
Phe Leu Asn Glu Leu Asn Thr Met Pro Gly Phe Thr Asp Phe Ser Met
305                 310                 315                 320
Tyr Pro Leu Leu Trp Glu Asn Met Gly Leu Lys Tyr Ser Asp Leu Ile
                325                 330                 335
Glu Glu Leu Ile Gln Leu Ala Leu Asn Arg Phe Lys
             340                 345
```

PROTEIN CONFERRING AN INDUCIBLE RESISTANCE TO GLYCOPEPTIDES, PARTICULARLY IN GRAM-POSITIVE BACTERIA

The invention relates to the polypeptides associated with the expression of a resistance to antibiotics of the glycopeptide family, this resistance being of a type inducible by vancomycin and not inducible by teicoplanin, particular in the Gram-positive bacteria, in particular in the family of the Gram-positive cocci. The invention also relates to a nucleotide sequence coding for these polypeptides. It also relates to the use of these polypeptides and their nucleotide sequence as agents for the in vitro detection of resistance to glycopeptides. Among the Gram-positive cocci, the invention relates more particularly to the enterococci, the streptococci and the staphylococci.

The glycopeptides, which include vancomycin and teicoplanin, are antibiotic inhibitors of the synthesis of the bacterial cell wall. These antibiotics are very much used for the treatment of severe infections due to Gram-positive cocci (enterococci, streptococci and staphylococci) in particular in cases of allergy and resistance to the penicillins.

Up to 1986 vancomycin proved to be efficacious against almost all strains of enterococci.

The activity of the glycopeptides depends on the formation of a complex between the antibiotic and the peptidoglycan precursors more than on their direct interaction with enzymes of cell wall metabolism. In particular, it has been observed that the glycopeptides bind to the terminal D-alanyl-D-alanine (D-ala-D-ala) residues of the peptidoglycan precursors.

Several phenotypes of resistance to the glycopeptides have been demonstrated; in particular, strains resistant to a high level of glycopeptides and strains resistant to low concentration levels.

By strain resistant to a high level is meant a strain of bacteria, in particular a strain of Gram-positive cocci, for which the minimal inhibitory concentrations (MIC) of vancomycin and teicoplanin are higher than 32 and 8 $\mu$g/ml, respectively. The MIC of vancomycin towards strains with low-level resistance are included between 8 and 32 $\mu$g/ml. The VanB phenotype is characterized by a resistance inducible by vancomycin but not inducible by teicoplanin. Once induced, this resistance may exist against different glycopeptides, in particular against vancomycin and/or teicoplanin, and at variable levels.

The strains of enterococci corresponding to the VanB phenotype (class B) are in particular strains of *E. faecalis* and *E faecium*.

Al-Obed S et al. (FEMS Microbiology Letters 70 (1990) 101–106) have thus compared the resistance proteins to glycopeptides, inducible by vancomycin, in four strains of Enterococci, and have deduced from their comparison the existence of three types of proteins, one of these types being present in the *E. faecium* strain resistant to low levels of vancomycin. According to the authors of this publication, a protein of molecular weight of about 39.5 kDa is induced in the strains with low-level resistance and this resistance is linked to induction by vancomycin. These strains were also reported to exhibit a resistance to teicoplanin, also induced by vancomycin.

According to Al-Obeid et al., this protein of 39.5 kDa is present in multiple forms but the nature of this multiplicity has not been studied. According to these authors there might exist a structural specificity depending an the species of bacteria concerned and the level Of resistance, which needs to be confirmed.

In this publication Al-Obeid et al. described 11 amino acids of the N-terminal sequence of the protein of 39.5 kDa and observed that this sequence exhibited about 70% homology with many membrane proteins of prokaryotic or eukaryotic origin having diverse functions. According to the authors this comparison did not allow the possible function of the protein to be established. Finally, Al-Obeid et al. noticed that other proteins are induced, although to a lesser degree.

The invention relates to peptides, polypeptides or proteins implicated in the expression of a resistance to antibiotics of the glycopeptide family and in particular to vancomycin and/or teicoplanin as well as nucleotide sequences coding for such polypeptides. The resistance in question above is of a type inducible by vancomycin but not by teicoplanin.

The expressions "implicated in the expression of a resistance" or "implicated in a resistance" signify that the protein of the invention is necessary in order for the resistance to be manifest.

The invention also relates to nucleotide probes utilizable for the detection of a resistance to the glycopeptides, in particular by means of the polymerase chain reaction (PCR), or y assays involving antibodies.

Thus, the object of the invention is a VanB protein characterized in that it comprises the amino acid sequence I (SEQ. ID NO:2), and in that it participates in the resistance to glycopeptides, in particular to vancomycin, this resistance being of a type inducible by vancomycin and not by teicoplanin in Gram-positive bacteria By the expression "inducible resistance" is meant the capacity of a specific Gram-positive bacterium, in particular of a specific Enterococcus strain, to produce a VanB protein in the presence of a concentration of 0.05 to 1 $\mu$l/ml of vancomycin.

The resistance to one or more defined glycopeptides may result in the persistence of an infection due to microbes usually sensitive to the glycopeptides, or may be detected by means of an antibiogram (particularly for high levels of resistance), the MIC, hybridization with probes (after amplification by the PCR, for example).

According to a first embodiment of the invention, the VanB protein is characterized in that it is implicated in an inducible resistance to glycopeptides, and in particular to vancomycin, in enterococci and for example in strains of the genus *E. faecium* or *E. faecalis*.

The invention also relates to a VanB protein characterized in that it comprises an amino acid sequence modified with respect to sequence I by deletion, insertion, or replacement of one or more amino acids, provided that the VanB protein thus modified is implicated in Gram-positive bacteria in a resistance to glycopeptides, in particular to vancomycin, this resistance being of a type inducible by vancomycin, but not inducible by teicoplanin Also included in the framework of the invention is any peptide fragment of the VanB protein characterized in that it corresponds to the amino acid sequence I or any part of this sequence functionally associated with the inducible resistance to glycopeptides, in particular to vancomycin, in Gram-positive bacteria, for example bacteria of the family of the enterococci.

Advantageously peptide fragments of the invention exhibit additionally or alternatively antigenic properties and are hence recognized by antibodies formed against the VanB protein.

A particular fragment of sequence I corresponds for example to the sequence of residues 110–305 of SEQ. ID NO:2 or includes the sequence of residues 110–305 of SEQ. ID NO:2.

According to another embodiment of the invention, these antigens are specific for the VanB protein and thus not recognized by antibodies recognizing the VanA and VanC proteins such as described in the patent application EP 91920753.

In addition the invention relates to a nucleotide sequence characterized in that it codes for a VanB protein implicated in resistance to glycopeptides, in particular to vancomycin, in Gram-positive bacteria, this resistance being of a type inducible by vancomycin but not inducible by teicoplanin, said VanB protein comprising the amino acid sequence I or in that it is a DNA sequence complementary to this coding sequence or a corresponding RNA sequence.

By complementary sequence is meant any DNA sequence whose nucleotides are complementary to those of sequence I and whose orientation is reversed.

A particular nucleotide sequence corresponding to this definition is characterized in that it comprises the following nucleotide sequence II or a nucleotide sequence modified with respect to II provided that it codes for a protein implicated in resistance to glycopeptides, in particular to vancomycin, in Gram-positive bacteria, this resistance being of a type inducible by vancomycin but not inducible by teicoplanin. SEQ. ID NO:1) GAGCGTGTGCTGC-GAGATACCACAGAAAACAATCAGAAT-TGTCTTAACTTTGAAA GGAGTTTACAGCATGAATAAAATAAAAGTCGCAA-TTATCTTCGGCGGTT- GCTCGG AGGAACATGATGT-GTCGGTAAAATCCGCAATAGAAATTGCT-GCGAACATTAATAC TGAAAAATTCGATCCGCACTA-CATCGGAATTACAAAAAACGGCGTATGGAAGCTA TGCAAGAAGCCATGTACGGAATGG-GAAGCCGATAGTCTCCCCGCCATATTCTCCC CGGATAGGAAAACGCATGGTCTGCTTGT-CATGAAAGAAAGAGAATACGAAACTCG GCGTAT-TGACGTGGCTTTCCCGGTTTTGCATG-GCAAATGCGGGGAGGATGGTGCG ATACAGGGTCTGTTTGAATTGTCTGG-TATCCCCTATGTAGGCTGCGATATTCAAA GCTCCG-CAGCTTGCATGGACAAATCACTGGCCTA-CATTCTTACAAAAAATGCGGG CATCGCCGTCCCCGAATTTCAAATGAT-TGAAAAAGGTGACAAACCGGAGGCGAGG ACGCT-TACCTACCCTGTCTTTGTGAAGCCG-GCACGGTCAGGTTCGTCCTTTGGCG TAACCAAAGTAAACAGTACGGAAGAAC-TAAACGCTGCGATAGAAGCAGCAGGACA ATAT-GATGGAAAAATCTTAATTGAGCAAGC-GATTTCGGGCTGTGAGGTCGGCTGC GCGGTCATGGGAAACGAGGAT-GATTTGATTGTCGGCGAAGTGGATCAAATCCGGT TGAGCCACGGTATCTTCCGCATCCAT-CAGGAAAACGAGCCGGAAAAAGGCTCAGA GAAT-GCGATGATTATCGTTCCAGCAGACATTC-CGGTCGAGGAACGAAATCGGGTG CAAGAAACGGCAAAGAAAG-TATATCGGGTGCTTGGATGCAGAGGGCTTGCTCGTG TTGATCTTTTTTTGCAGGAGGATGGCG-GCATCGTTCTAAACGAGGTCCAATACCC TGCCCG-GTTTACATCGTACAGCCGCTATCCACG-CATGGCGGCTGCCGCAGGAAT CACGCTTCCCGCACTAATTGACAGCCT-GATTACATTGGCGATAGAGAGGTGACCC GTATG-GAAAATGGTTTTTTGTTTTTTAGATGAAATGTTGCA Generally speaking the sect of the invention is also a nucleotide fragment characterized in that it is capable of hybridizing under stringent conditions with a sequence such as defined in sequence II above, The stringent conditions are the following:
reaction temperature of 65° C. overnight in a solution containing 0.1% SDS, 0.7% skimmed milk powder, 6×SSC (1×SSC=0.15M NaCl and 0.015M sodium citrate at pH=7.0) washes at room temperature in 2×SSC-0.1% SDS, then at 65° C. in 0.2 SSC-0.1% SDS.

Advantageously a nucleotide fragment corresponding to the previous definition will have at least 15 nucleotides, and preferably at least 20.

For this purpose a particular nucleotide sequence comprises the following sequence: (SEQ. ID NO:3) TCTGTTTGAATTGTCTGGTATCCCCTAT-GTAGGCTGCGATATTCAkz GCTCCGCAGCTTG-CATGGACAAATCACTGGCCTACATTCT-TACAAAAAATGCGGG CATCGCCGTCCCCGAATTTCAAATGAT-TGAAAAAGGTGACAAACCGGAGGCGAGG ACGCT-TACCTACCCTGTCTTTGTGAAGCCG-GCACGGTCAGGTTCGTCCTTTGGCG TAACCAAAGTAAACAGTACGGAAGAAC-TAAACGCTGCGATAGAAGCAGCAGGACA ATAT-GATGGAAAAATCTTAATTGAGCAAGC-GATTTCGGGCTGTGAGGTCGGCTGC GCGGTCATGGGAAACGAGGAT-GATTTGATTGTCGGCGAAGTGGATCAAATCCGGT TGAGCCACGGTATCTTCCGCATCCAT-CAGGAAAACGAGCCGGAAAAAGGCTCAGA GAAT-GCGATGATTATCGTTCCAGCAGACATTC-CGGTCGAGGAACGAAATCGGGTG CAAGAAACGGCAAAGAAAG-TATATCGGGTGCTTGGATGCAGAGGGCTTGCTCGTG TTGATCTTTTTTTGCAGGAGGATGGCG-GCATCGTTCTAAACGAGGTC The peptides and polypeptides of the invention make it possible to define a genotypic class, characterized by the capacity of the nucleotide sequences coding for these peptides to hybridize under stringent conditions with the sequence II constituting a probe.

These fragments may be used as primers for carrying out amplification reactions, or as probes.

Particularly valuable probes correspond to the following sequences: (SEQ. ID NO:4–5)
primer 1:5' ATGGGAAGCCGATAGTC 3' (SEQ. ID NO:4) (positions 241–258 of nucleotides of sequence I)
primer 2:5' GATTTCGTTCCTCGACC 3' (SEQ ID NO:5) (complementary reverse sequence of the nucleotide fragment 860–877 of sequence I).

Nucleotide probes according to the invention may be specific for the detection in Gram-positive bacteria of sequences coding for a VanB protein implicated in the resistance to glycopeptides, in particular to vancomycin and/or teicoplanin, this resistance being inducible in conformity with the previous definition, these probes being in addition universal among these sequences.

By probes specific for VanB is meant any oligonucleotide hybridizing with a nucleotide sequence coding for a VanB protein according to the invention as described in the preceding pages, and not exhibiting cross-hybridization or amplification (PCR) reactions with sequences present in all of the sensitive strains.

A particular nucleotide fragment according to the invention is characterized in that it does not hybridize under stringent conditions with the DNA of strains of enterococci sensitive to vancomycin, in particular with the DNA of the strains E. faecalis JH2—2 and E. faecium BM4107.

These reference strains have been described by Jacobs and Hobbs (J. Bacteriol. 117, 1974, 360–372) and Leclercq et al. (Antimicrob. Agents Chemother. 33, 1989), respectively.

Another useful nucleotide fragment in the framework of the invention is specific for the vanB gene to the extent that it does not hybridize under stringent conditions with the vanA and vanC genes as described in the PCT application 91920753.

A particularly useful nucleotide fragment in the framework of the invention is the fragment corresponding to sequence II.

This fragment is an internal fragment derived from the gene implicated in the resistance to strains of enterococci. The resistance may exist at variable concentration levels of glycopeptides The invention also relates to nucleotide fragments modified with respect to the foregoing by mutation, addition or deletion of nucleotides, provided that the fragment thus modified either codes for a fragment of the functional VanB protein as regards its property of the resistance to glycopeptides, in particular to vancomycin, under conditions described above, or hybridizes with the vanB gene.

Should the nucleotide fragments be used as probes, labelling is performed by the standard techniques. As examples, radioactive or enzymatic markers should be used.

Nucleotide fragments according to the invention may be used as primers to carry out the amplification of the nucleic acid contained in a given biological sample, for example by PCR Moreover, the invention relates to a recombinant DNA sequence characterized in that it comprises a nucleotide sequence described above under the control of regulatory elements likely to be involved in the cloning and expression of a gene implicated in a resistance, of a type inducible by vancomycin and not inducible by teicoplanin, to antibiotics of the glycopeptide family, in particular vancomycin, in a defined host.

This gene implicated in the resistance is for example the vanB gene which comprises the nucleotide sequence II or any functional part in terms of inducible resistance derived from a sequence hybridizing with sequence II.

The invention also relates to a recombinant vector for the cloning and expression, characterized in that it comprises a nucleotide sequence described above at a site inessential for its replication, optionally under the control of regulatory elements likely to be involved in the expression of a resistance, of a type inducible by vancomycin and not by teicoplanin, to antibiotics of the glycopeptide family, in particular vancomycin, in a defined host.

Particular vectors are for example plasmids, phages, cosmids, YACs.

A preferred vector is the plasmid pAT201 deposited with the C.N.C.M. on 11 Dec. 1992 under the number I-1277.

Another preferred vector is the plasmid pAT202 formed from the plasmid pUC19Ω containing a 3.3 kb fragment containing the vanB gene of *Enterococcus faecalis* V583 (HindIII/KpnI).

pAT202 was introduced into *E. coli* JM83 and deposited with the C.N.C.M. on 29 Mar. 1993 under the number I-1291 (identification *E. coli* BM2973).

These vectors may be used to transform or transfect cell hosts in order to clone or express the nucleotide sequences of the invention.

A recombinant cell host according to the invention is characterized in that it is modified by a nucleotide sequence or a vector described above.

The cell host is preferably modified by this sequence under conditions permitting the expression of a functional VanB protein as regards inducible resistance to glycopeptides.

The object of the invention is also a recombinant VanB protein such as obtained from a recombinant cell host according to the previous definition, the VanB protein obtained being characterized in that its peptide skeleton comprises the above amino acid sequence, and in that it is implicated in a resistance to glycopeptides, in particular to vancomycin, in Gram-positive bacteria, this resistance being of a type inducible by vancomycin but not inducible by teicoplanin.

The VanB protein according to the invention makes it possible to prepare monoclonal or polyclonal antibodies characterized in that they recognize specifically the VanB protein or a peptide fragment described above.

These antibodies may be obtained according to the standard methods for the production of antibodies. In particular for the preparation of the monoclonal antibodies recourse should be had to the method of Köhler and Milstein according to which monoclonal antibodies are prepared by cell fusion between myeloma cells and spleen cells of mice previously immunized with a polypeptide or a composition according to the invention, in conformity with the standard procedure The antibodies of the invention can advantageously be used for the detection of the presence of proteins characteristic of a resistance to the glycopeptides, in particular to vancomycin and teicoplanin, this resistance being of the type inducible by vancomycin but not inducible by teicoplanin.

Also included in the framework of the invention is a kit for the in vitro diagnosis in a biological sample of the presence of strains resistant to glycopeptides after induction, in particular by vancomycin but not by teicoplanin, these strains belonging in particular to the Gram-positive cocci, in particular in that they are strains of enterococci, for example *E. faecium*, characterized in that it contains:

optionally labelled antibodies described above, a reagent for the detection of an immunological reaction of the antigen-antibody type, optionally, reagents for lysing the cells of the tested sample, optionally, a defined concentration of vancomycin to induce resistance.

The invention also relates to a kit such as that defined above which contains in addition antibodies specifically directed against the VanA protein and/or antibodies specifically directed against the VanC protein.

According to another embodiment of the invention, the kit enables resistance corresponding to a phenotype VanA VanB or VanC to be detected indiscriminately and contains antibodies recognizing VanA, VanB and VanC These antibodies may be selected by their capacity to recognize an epitope common to the three proteins. It may also be a mixture of antibodies recognizing different epitopes, specific to each of the proteins.

According to another embodiment of the invention, a kit for the in vitro diagnosis of the presence of strains resistant to low levels of glycopeptides, resistant in particular to vancomycin, is characterized in that it contains:

a nucleotide probe capable of hybridizing under stringent conditions with a nucleotide sequence of the vanB gene, and optionally, nucleoside triphosphates dATP, dCTP, dTTP, dGTP, a DNA plymerase.

Another detection kit contains in addition nucleotides capable of hybridizing specifically with the vanA gene and a probe capable of hybridizing specifically with the vanC gene.

This kit may be advantageously used for the detection of a resistance in Gram-positive cocci, in particular in enterococci, for example in E. faecium.

The invention also relates to a kit for the in vitro detection of a resistance to glycopeptides, in particular to vancomycin, this resistance corresponding to one of the phenotypes VanA, VanB or VanC, the kit containing:

a nucleotide probe hybridizing with the genes vanA, vanB and vanC, nucleoside triphosphates dATP, dCTP, dTTP and dGTP, a DNA plymerase.

The invention also relates to a procedure for the in vitro detection of the presence of strains resistant to glycopeptide in particular to vancomycin and/cr teicoplanin, these strains belonging in particular to the family of the Gram-positive cocci, in particular in that they are strains of enterococci, for example E faecium or E. faecalis, characterized in that it comprises:

a) the placing of a biological sample likely to contain the resistant strains in contact with a primer constituted by a nucleotide fragment according to the invention such as that described above, capable of hybridizing with the nucleotide sequence under investigation and implicated in the expression of the resistance, this sequence being used as matrix in the presence of the 4 different nucleoside phosphates and a polymerase under conditions of hybridization such that for each nucleotide sequence having hybridized with a primer, an elongation product of each primer complementary to the matrix is synthesized, b) the separation of the matrix from the elongation product obtained, this latter being then also able to behave as a matrix, c) repetition of step a) so as to obtain a detectable quantity of the nucleotide sequences investigated, d) the detection of the amplification product of the nucleotide sequences.

The probe used may thus be specific for the nucleotide sequence II or a sequence hybridizing with sequence II under stringent conditions. Under these conditions, the procedure according to the invention makes possible the detection of a resistance to glycopeptides, this resistance being inducible by vancomycin but not inducible by teicoplanin.

According to a particular embodiment of the invention, this procedure also comprises the placing of the biological sample in contact with a specific nucleotide fragment of the vanA gene and/or a specific nucleotide fragment of the vanC gene. In this case the procedure according to the invention advantageously makes possible the detection of different phenotypes of resistance.

According to another embodiment, a resistance corresponding to a phenotype VanA, VanB Cr VanC will de detected indiscriminately by using a probe common to the genes vanA, vanB or vanC. Such a probe may be constructed from the aligned polypeptide sequences of FIG. 2.

Other characteristics and advantages of the invention will become apparent in the following Examples and Figures:

FIGURES

FIG. 1

Nucleotide and amino acid sequences corresponding to the vanB gene (SEQ. ID NO:1–2). The nucleotide sequences of the two strands was determined from the insert contained in pUC18 by the dideoxy chain termination method (Sanger et al., 1977, Proc. Natl. Acad. Sci. USA, 74: 5463–5467) using T7 DNA polymerase. The RBS sequence underlined represents the Shine-Dalgarno sequence for ribosome binding.

FIG. 2

Alignment of the deduced amino aid sequence of the VanB protein and corresponding regions of VanA, VanC, DdLA and DdLB of E. coli (Dutka-Malen et al., 1992 Gene, 112: 53–58), Ddl of E. faecalis V583 and DdlA of S. typhimurium (Daub et al., Biochemistry 27 1988 3701–3708) (SEQ. ID NO:2, 6–11). The identical amino acids (I) and the conservative substitutions (C) in the 7 sequences have been indicated beneath the alignment. In order to permit the classification of conservative substitutions, the amino acids have been regrouped as follows: RK, LFPMVI, STQNC, AGW, H, ED and Y The domains 1, 2, 3 and 4 correspond to regions of high homology.

FIG. 3

Oligonucleotides V1 and V2 used to amplify the DNA of the vanB gene (SEQ. ID NO:12–15).

FIG. 4

Nucleotide sequence of the ddl gene of E. faecalis V583 and the corresponding amino acid sequence (SEQ. ID NO:16–17). The plasmid pAT203 was constructed by subcloning the DNA of λ recombinant bacteriophage partially digested with Sau3AI (Pharmacia) in pUC19 digested with BamHI (Pharmacia). The 15 kb insert of pAT203 contains the ddl gene. The nucleotide sequence of 1079 consecutive bp of pAT203 was determined on both strands by the dideoxy chain termination method. The first base pair of the sequence is defined as position 1. The ribosome binding sequence RBS is at position 19 upstream from the start codon TTG The stop codon TTA is indicated. The deduced amino acid sequence of the Ddl protein is shown.

EXPERIMENTAL APPROACH

The antibiotics of the glycopeptide family such as vancomycin (Vm) and teicoplanin (Te) bind to the C-terminal D-Ala residues of the peptidoglycan precursors thus blocking their incorporation into the bacterial cell wall (Reynolds, P.E. 1989 Eur. J. Qin. Microb Infect. Dis. 8: 943–950). The D-Ala residues are incorporated into the precursors of the cell wall in the form of dipeptides synthesized by D-Ala:D-ala ligases (DDL) (Walsh, C.T. 1989 J. Biol. Chem. 264: 2393–2396). The VanA ligase synthesizes the dipeptide D-Ala-D-lac which substitutes for D-Ala-D-Ala leading to the synthesis of precursors which bind vancomycin with reduced affinity (Bugg et al., Biochemistry 30: 10408–10415 (1991), Handwerger et al., J. Bacteriol. 174: 5982–5984 (1992), Messer et Reynolds, FEMS Microbid. Letters 94: 195–200 (1992)).

The resistance to the glycopeptides in the enterococci is heterogeneous (Dutka-Male et al., 1990 Antimicrobiol Agents Chemother. 34: 1875–1879).

The resistance proteins VanA and VanC (see patent application EP 91920753.0 of 29 Oct. 1991) show a 30 to 37% homology (the details are given in Table III) with the amino acids of the D-Ala: D-Ala ligases (Ala=alanine) of E. coli (Dutka-Malen et al., 1992 Gene 112: 53–58). The structural genes for the VanA and VanC proteins do not hybridize with the DNA of the strains with the VanB phenotype (Dutka-Malen et al., 1990, Leclercq et al., Antimicrob Agents Chemother. 36: 2005–2008 (1992)).

The inventors have succeeded in identifying the nucleotide sequence implicated in the properties of resistance to vancnycin of strains of enterococci having the VanB phenotype and resistant after induction with vancomycin.

Bacterial strains: 39 isolates of *E. faecium* (28 strains) and *E faecalis* (11 strains) resistant to low and high concentrations of vancomycin and sensitive to teicoplanin were studied (Table II). Among these strains 24 isolates including *E. faecalis* V583 (Sahm D. Et al., Antimicrob. Agents Chemother. 1989, 33: 1588–91) and *E faecium* D366 (Gutmann L. Et al., Antimicrob. Agents Chemother. 1992, 36: 77–80) were resistant to low concentrations of vancomycin on the basis of a disk sensitivity test. These strains belong to the class B phenotype. 15 isolates resistant to high concentrations of vancomycin (MIC $\geq 128$ μg/ml) including *E. faecalis* strain V583-2 (Zarlenga LJ. Et al., Antimicrob. Agents Chemother. 1992, 36: 902–5), which is a spontaneous mutant of V553 as well as UMH-1 (Schwalbe R. Et al., Abstract A-117, in Abstracts of the 91st General Meeting of the American Society for Microbiology, Dallas, Tex. American Society for Microbiology, 1991) were also studied. The control strains were well-characterized strains of enterococci belonging to the phenotypes A and C and hybridizing with the probes VanA and VanC, respectively. In particular there are 6 clinical isolates of *E. faecium* highly resistant to vancomycin and to teicoplanin, including BM4147. The strains of *E. gallinarum* including BM4147 belonging to class C were also used as controls. Strains of *E. casseliflavus* are also used as controls, including the strain ATCC 25788, which are isolates intrinsically resistant to low levels of vancomycin and sensitive to teicoplanin (Leclercq R et al., Antimicrob. Agents Chemother. 1992, 36: 2005–8).

The following strains were also studied: *Erysipelothrix rhusiopathiae* A124 (Institute Pasteur collection), *Lactobacillus brevis* ATCC 14869, *Lactobacillus casei* ATCC 393, *Lactobacillus confusus* ATCC 10881, *Lactobacillus fermentum* ATCC 9338, *Lactobacillus plantarum* ATCC 8014, *Lactobacillus reuteri* ATCC 23272, *Lactobacillus rhamnosus* ATCC 7469, *Lactobacillus salivarius* ATCC 11741, *Pediococcus acidilacti* ATCC 8042, *Pediococcus pentosaceus* ATCC 33316, and *Leuconostoc mesenteroides* CIP 16407. The following enterococci sensitive to antibiotics of the glycopeptide family are used as negative controls: *E. durans* ATCC 19432, *E. faecium* ATCC 19434, BM4107 (Leclercq R et al., Antimicrob. Agents Chemother. 1992, 36: 2005–8), and MT10R (Gutmann L et al., Antimicrob. Agents Chemother., 1992, 36: 77–80), strain sensitive to vancomycin derived from D366; *E. faecalis* ATCC 29212, ATCC 33186, JH2-2 (Leclercq R et al., Antimicrob. Agents Chemother. 1992, 36: 2005–8) and V583-C1, strain sensitive to vancomycin derived from V583 (Table II) and a clinical isolate of *E. faecium* and *E. faecalis*. Characteristics of reference strains are depicted in Table I. *E. faecium* BM4107 and *E. faecalis* JH2-2, resistant to both rifampin and fusidic acid (Leclercq R et al., Antimicrob. Agents Chemother. 1992, 36: 2005–8) were used as receptor strains for conjugation experiments.

Identification of the enterococci

The enterococci were identified by the method of Facklam and Collins, J. Qin. Microbiol. 1989, 27: 731–4). The identification of the species was based on the tests of potassium tellurite reduction and the production of acids from carbohydrates on bands of API 20 streptococci (bioMérieux, Marcy l' Etoile France). The tests of mobility at 30° C. and fermentation of carbohydrates were used to distinguish *E. gallinarum* and *E. Casseliflavus* from *E. faecium* and *E. faecalis*. The strains of *E. Casseliflavus* were distinguished from the strains of *E. gallinarum* on the basis of the production of a yellow pigment on the agar.

Medium

A brain-heart medium and agar (Difco Laboratories, Detroit, Mich.) were used. Sensitivity tests were performed an Mueller-Hinton agar (Diagnostics Pasteur, Marne LaCoquette, France). All of the incubations were performed at 37° C.

Determination of the in vitro sensitivity to the antibiotics.

The disk diffusion test with disks containing 30 μg of vancomycin or 30 μg of teicoplanin (Diagnostics Pasteur) was used for the initial screening. The method of Steers et al. with $10^4$ CFU per spot was used to determine the MIC of the antibiotics (Steers E. Et al., Antibiot. Chemother. (Basel) 1959, 9: 307–11)

Transfer of the character of resistance to an antibiotic

The conjugation on filters was carried out according to the procedure described by Dutka-Malen S. Et al., Antimicrob. Agents Chemother. 1990, 34: 1875–9. The antibiotic concentrations for the selection of the transconjugates were the following: rifampin: 20 μg/ml; fusidic acid: 10μg/ml and vancomycin: 4 and 8 μg/ml.

Enzymes and reagents

Lysozyme was obtained from the Sigma Chemical Co.(St. Louis, Mo.). RNase A (bovine pancreas) and proteinase K were obtained from Calbiochem. Co.(San Diego, Calif.). {α-32p} dCTP and the triethylammonium salt (specific activity 3000 CI/mmol) were obtained from the Radiochemical Center, Amershan, Great Britain. Teicoplanin was obtained from Gruppo Lepetit (Milan, Italy) and vancomycin was obtained from Eli Lilly & Co (Indianapolis, Ind.).

The oligonucleotides V1 and V2 described in the patent application EP 91920753.0 made possible the amplification by means of the PCR technique of fragments internal to the genes coding for the proteins VanA, VanC and D-Ala: D-Ala ligases (Dutka-Malen et al., 1992 Gene 112: 53–58).

The amplification of the vanB gene was carried out with the oligonucleotides V1 and V2 and the DNA (20 ng) of *Enterococcus faecalis* V583 (Sahm et al., 1989 Antimicrob. Agents Chemother.33: 1588–1591).

To carry out this amplification the technique described in the publication of Dutka-Malen et al., 1992 was used. The fragments obtained were separated on agarose gel (1%) in a TAE buffer which made it possible to reveal a unique band of about 600 bp which was extracted from the gel using a DNA purification kit (GeneClean, Bio101 Inc, La Jolla, Calif.). By using a kit leading to the production of blunt ends an the DNA (Amersham, Amersham, Great Britain), the fragments were treated with the T4 DNA polymerase and ligated at the SmaI site of a digested and dephosphorylated pUC18 plasmid (Norrander et al., 1983, Gene 26: 101–106).

The sequence of 632 bp (vanB probe) corresponding to the insert of the recombinant plasmid (FIG. 1) was determined by the dideoxy chain termination method (Sanger et al., 1977, Proc Natl. ACad. Sd. USA 74: 5463–5467) using T7 DNA polymerase (Pharmacia, Uppsala, Sweden) and {α-$^{35}$S} dATP (Amersham Radiochemical Center, Amersham, Great Britain).

Given that the amplification with the Taq DNA polymerase may lead to erroneous incorporations of nucleotides, the sequence was confirmed as follows: an oligonucleotide complementary to the positions 513 to 530 of the nucleotide sequence shown in FIG. 1 was synthesized by the phosphoramidite method (Organic Chemistry unit, Pasteur Institute, France) and used with the primer V1 to carry out an amplification of a vanB fragment by PCR. The PCR product was sequenced directly (Mabilat et al., 1990, Plasmid 23: 27–34) or after the cloning in a pUC18 vector in order to reveal the identity of the nucleotides with the cloned fragment obtained with V1 and V2.

A Southern hybridization was carried out according to the method of Johnson et al., Gene Anal. Technol. 1: 3–8 (1984). The total DNA of the strains of enterococci (Table 1) was prepared according to the procedure described by Le Bouguenec et al., 1990, J. Bacteriol. 172: 727–734, digested with the enzymes HindIII and KpnI (United States Biochemical corporation, Cleveland, Ohio) and resolved on 1% agarose gels. The DNA was transferred to nylon membranes (Nytran, Schleicher & Schuell, Dassel, Germany) with a transfer apparatus under vacuum (Trans. Vac. TE80, Hoefer Scientific Instruments, San Francisco, Calif.). The probe was obtained by labelling the cloned PCR fragment with a nick translation kit (Bethesda Research Laboratories Life Technologies Inc, Gaithersburg, Md.) and $\{\alpha\text{-}^{32}p\}$ dCTP (Amersham Radiochemical Center, Amersham, Great Britain). The hybridization was carried out under stringent conditions at 68° C. (Johnson et al., 1984, Gene Anal. Technol. 1: 3–8). The membranes were washed at 65° C. in 0.1% SDS-2×SSC The vanA probe consisted of a PstI fragment of 265 bp internal to the vanA gene (Dukta-Malen S et al., Mol. Gen. Genet. 1990, 224: 364–372). The vanC probe consisted of a EcoRI-HincII fragment of 690 bp internal to the vanC gene (Leclercq R et al., Antimicrob. Agents Chemother. 1992, 36: 2005–8. Dukta-Malen S. Et al. Gene, 1992, 112: 53–58). The vanB probe corresponds to the sequence II.

The amino add sequence deduced for the insert contained in the pUC18 plasmid was compared with different protein sequences (FIG. 2): Table 5 sunmarises the identity percentages of amino acids when the protein sequences VanB, VanA, VanC ElDdl, DdlA and DdlB are compared pairwise. Under the conditions of Southern hybridization the cloned fragment hybridized with the 3.3 kb HindIII-KpnI fragment of E. faecalis V583. The probe does not hybridize with the DNA of a vancomycin-sensitive derivative of V583 or with the DNA of the E. faecalis and E. faecium strains sensitive to vancomycin used as reference. The cloned DNA fragment obtained by PCR corresponds to an internal fragment of the gene implicated in the resistance. This gene codes for the enzyme related to the D-Ala: D-Ala ligases, called VanB, which might be implicated in the synthesis of a product substituting for D-Ala-D-Ala.

These tests have made it possible to demonstrate a single group of genes related to vanB and responsible for a low- and high-level resistance to vancomycin in the enterococci (Tables 1 and 2).

No hybridization was observed between the VanB probe and the DNA of strains sensitive to vancomycin without induction or bearing the vanA or vanC genes or intrinsically resistant.

The complete sequence of the vanB gene was cloned by implementing the following steps:

The plasmid pAT202 was obtained by subcloning in pUC19 a 3.3 kb HindIII-KpnI fragment of the λ recombinant bacteriophage containing the vanB gene. The cloning was performed with restriction endonucleases (Boehringer, Mannheim, Germany and Pharmacia LKB Biotechnology Inc Uppsala, Sweden), T4 DNA ligase (Boehringer) and alkaline phosphatase (Pharmacia) in conformity with the recommendations of the manufacturer. The nucleotide sequence of the consecutive 1090 bp of pAT202 was determined on both strands by the dideoxy chain termination method (Sanger et al., 1977) using a modified T7 DNA polymerase (Amersham Radiochemical Center, Amersham, Great Britain) and complementary oligonucleotides of the sequence, synthesized by the methoxy phosphoramidite method (Institute Pasteur, Paris, France). The reaction products were resolved by electrophoresis on a 6% denaturing polyacrylamide gel. The first base pair of the sequence shown corresponds to position 1 (FIG. 1). The potential ribosome binding site (RBS) (Moran et al., Md. Gen. Genet. 186 (1982) 339–346) upstream from the ATG initiation codon at position 46 is underlined. The stop codon (TGA) is indicated by an asterisk. The amino acid sequence is aligned with the first nucleotide of each codon.

The transfer of the vancomycin-resistance character (in 6 isolates of enterococci out of 17) by conjugation on a filter was observed in E. faecium and E. faecalis strains resistant to low or high concentrations of antibiotics.

Of the other fragments of about 600 bp amplified from the oligonucleotides V1 and V2, an insert hybridized with the DNA of $Vm^R$ or $Vm^S$ strains of E. faecalis but not with the DNA of strains of 18 other species. This gene codes for a D-Ala: D-ala ligase in E faecalis. Since no other ligase gene was detected in E. faecalis, this gene was called ddl.

The cloning and sequencing of the ddl gene inserted in the pUC19 vector (Norrander et al., Gene 26, 1983, 101–106) led to the observation that the content of the bases G and C in ddl (37.5%) and the chromosome of E. faecalis (37–39%) were very similar.

Different observations suggest that the vanB gene might have an exogenous origin: (i) The gene may be transferred by conjugation. (ii) The nucleotide sequences related to vanB have not been detected in the DNA of $Vm^S$ strains of E. faecalis and E faecium and the representatives of 16 other species of Enterococcus (Table III). (iii) The GC base content of the vanB gene differs markedly from that of the chromosome of E. faecalis. (iv) The low level of similarity between Ddl of E. faecalis and VanB (34% identity) indicates that the corresponding genes have not originated as the result of a recent duplication.

Precursors of Peptidoglycan in E. faecalis $Vm^R$ and $Vm^S$

The incubation of E. faecalis V583 before the induction of the $Vm^R$ or $Vm^S$ strains of E faecalis JH2-2 (Jacob and Hobbs, J. Bacteriol. 117, 1974, 360–372) with the cell wall inhibitor ramoplanin (9 µg/ml) led to the accumulation of the cell wall precursor UDP-N-acetyl-muramyl-L-Ala-D-Glu-L-Lys-D-Ala-D-Ala (UDP-Mur-NAc-pentapeptide) which is used in the normal cycle of peptidoglycan synthesis.

After the induction of resistance, E. faecalis V583 accumulated three cell wall intermediates when the strain was incubated with ramoplanin (Table IV). These intermediates were identified as being UDP-MurNAc-pentapeptides, UDP- MurNAc-tetrapeptides lacking the C-terminal D-Ala residue of the UDP-MurNAc-pentapeptide; and predominantly UDP-MurNAc-tetrapeptide-D-lactate in which the C-terminal D-Ala residue of the UDP-MurNAc-pentapeptide is replaced by D-lactate. The presence of UDP-MurNAc-tetrapeptide-D-lactate suggests that the strains of the VanA and VanB phenotypes have the same basic resistance mechanism to the glycopeptides; i.e. they synthesize D-lactate which may be linked to VanB (or VanA) by D-Ala to synthesize D-Ala-D-lactate which is then incorporated into the peptidoglycan precursor.

The wall precursors were purified by ion exchange chromatography and desalting by gel filtration. The identification was based on mass spectrometry (positive ion electrospray mass spectroscopy), a UV spectrum (for the uracil) automated amino acid analysis after hydrolysis for 4h and 24h (for muramic acid and the ratios of the amino acids) and the analysis by specific enzymatic reactions of the terminal residue carried out by reaction with D,D-carboxypeptidase of Actinomadura R39 (Messer and Reynolds, FEMS Micrcbiol. Letter 94, 1992, 195–200).

The total quantity of precursors accumulated in each culture was approximately the same. 65 µmol/g of dry weight during an incubation period corresponding to 0.6 of the mean synthesis time.

TABLE I

Bacterial strains

| Strain | MIC (μg/ml) Vm | Te | Hybridization with the vanB probe vanA | vanB | vanC | Reference |
|---|---|---|---|---|---|---|
| *E. faecalis* | | | | | | |
| V583 | 64 | 0,5 | − | + | − | Sahm et al (1989) |
| V583-C1 | 2 | 0,5 | − | − | − | D. F. Sahm |
| V583-2 | 1024 | 1,0 | − | + | − | Zarlenga L J (1992) |
| UMH-1 | 1024 | 1,0 | − | + | − | Schwalbe et al (1991) |
| ATCC 29212 | 2 | 0,5 | − | − | − | |
| *E. faecium* | | | | | | |
| D366 | 32 | 0,5 | − | + | − | Gutmann et al (1992) |
| MT10R | 2 | 0,25 | − | − | − | Gutmann et al (1992) |
| BM4147 | 1024 | 512 | + | − | − | Dutka-Malen et al (1990) |
| ATCC 19434 | 1 | 1 | − | − | − | |
| *E. gallinarum* | | | | | | |
| BM4174 | 8 | 1 | − | − | + | Dutka-Malen et al (1992) |
| *E. casseliflavus* | 8 | 1 | − | − | − | |

TABLE II

Phenotypic and genotypic classes among the Gram-positive cocci resistant to vancomycin

| PHENOTYPIC CLASS | GENOTYPIC CLASS (A) | SPECIES | MIC (μg/ml) Vancomycin | Teicoplanin |
|---|---|---|---|---|
| Susceptible | Susceptible | *Enterococcus spp.*(10) | 0.5–2 | 0.25 |
| A | A | *E.faecium*(6) | 256->1.000 | 64->1.000 |
| B | B | *E.faecium*(28) | 4–256 | 0.5–1 |
| B | B | *E.faecalis*(11) | 4–1024 | 0.5–1 |
| C | C | *E.gallinarum*(3) | 8 | 1 |
| C | NC | *E.casseliflavus*(2) | 4–8 | 0.5–1 |
| NC | NC | *Lactobacillus spp.*(8) | >1.000 | >1.000 |
| NC | NC | *Leuconostoc. sp.*(1) | >1.000 | >1.000 |
| NC | NC | *Pediococcus spp.*(2) | >1.000 | >1.000 |
| NC | NC | *E.rhusiopathiae*(1) | >1.000 | >1.000 |

(a)A: hybridization with the vanA probe; B: hybridization with the vanB probe
C: hybridization with the vanC probe; NC: not classed

TABLE III

Results of hybridization experiments

| Species | Resistance phenotype | Number of strains tested | Hybridization with probe vanB | ddl (*En. faecalis*) |
|---|---|---|---|---|
| *En. faecalis* | Vm$^R$, Te$^S$ | 11 | + | + |
| | Vm$^S$, Te$^S$ | 5 | − | + |
| *En. faecium* | Vm$^R$, Te$^R$ | 6 | − | − |
| | Vm$^R$, Te$^S$ | 28 | + | − |
| | Vm$^S$, Te$^S$ | 4 | − | − |
| *En. gallinarum* | Vm$^R$, Te$^S$ | 3 | − | − |
| *En. casseliflavus* | Vm$^r$, Te$^S$ | 2 | − | − |
| En. spp. (15 species[a]) | Vm$^S$, Te$^S$ | 15 | − | − |

[a]Types of strains *En. avium, En. cecorum, En. columbae, En. dispar, En. durans, En. flavescens, En. hirae, En. malodorarus, En. mundrii, En. pseudoavium, En. raffinosus, En. saccharolyticus, En. seriolicida, En. solitarius* et *En. sulfureus.*

TABLE IV

Peptidoglycan precursors in Vm$^S$ or Vm$^R$ strains of *En faecalis*

| Peptidoglycan precursor | Quantity of precursor (%) in *En faecalis* | | |
|---|---|---|---|
| | JH2-2 | V583 not induced | V583 induced |
| UDP—MurNAc—L—Ala—D—Glu—L—Lys—D—Ala—D—Ala | 100 | 100 | 14 |
| UDP—MurNAc—L—Ala—D—Glu—L—Lys—D—Ala | 0 | 0 | 7 |
| UDP—MurNAc—L—Ala—D—Glu—L—Lys—D—Ala—D—lactate | 0 | 0 | 79 |

TABLE V

Sequence identity between the amino acid sequnces of VanB, Ddl of *En. faecalis* V583 and D—Ala: D—Ala ligases[a]

| Compared sequence[b] | Percentage identity with respect to: | | | | | |
|---|---|---|---|---|---|---|
| | VanB | VanC | EfDdl | EcDdlA | StDdlA | EcDdlB |
| VanA | 76 | 38 | 32 | 38 | 37 | 30 |
| VanB | | 38 | 34 | 38 | 38 | 32 |
| VanC | | | 34 | 34 | 34 | 36 |
| EfDdl | | | | 40 | 40 | 34 |
| EcDdlA | | | | | 90 | 35 |
| StDdlA | | | | | | 36 |

[a]Identity of pairs of sequences derived from the alignment of FIG. 2
[b]Ec, *E.coli*; Ef, *En.faecalis*; St, *S.typhimurium*

---

What is claimed is:

1. A purified protein comprising the amino acid sequence of SEQ ID NO:2.

2. A purified nucleotide sequence encoding the amino acid sequence of SEQ ID NO:2.

3. A purified nucleotide sequence comprising the nucleotide sequence of SEQ ID NO:1.

4. A purified nucleotide sequence comprising the nucleotide sequence selected from the group consisting of SEQ ID NO:3, SEQ ID NO:4, and SEQ ID NO:5.

5. A vector selected from the group consisting of plasmid pAT201 deposited in the C.N.C.M. under accession number I-1277 and plasmid pAT202 deposited in the C.N.C.M. under accession number I-1291.

6. A purified protein comprising an amino acid sequence, wherein the amino acid sequence is encoded by the nucleotide sequence of SEQ ID NO:1, or the amino acid sequence is encoded by a first nucleotide sequence wherein a complement of the first nucleotide sequence hybridizes to a second nucleotide sequence comprising the nucleotide sequence of SEQ ID NO:1 if the complement of the first nucleotide sequence and the second nucleotide sequence are held together at 65° C. overnight in a solution containing 0.1%SDS, 0.7% skimmed milk powder, and 6X SSC, wherein the protein is synthesized in Gram-positive bacteria expressing a low level of resistance to vancomycin, wherein the resistance is not inducible by teicoplanin.

7. A purified peptide fragment of the protein of claim 6, wherein the peptide fragment comprises the amino acid sequence of residues 110–305 of SEQ ID NO:2.

8. The peptide fragment of claim 7, wherein the peptide fragment is recognized by an antibody to a VanB protein and not recognized by an antibody to a VanA or VanC protein.

9. A purified nucleotide sequence encoding the protein of claim 6.

10. The sequence of claim 9, wherein the sequence is RNA.

11. A purified nucleotide sequence complementary to the sequence of claim 9.

12. The sequence of claim 11, wherein the sequence is chemically or radioactively labeled.

13. A purified DNA sequence comprising (a) a gene coding for the protein of claim 6, and (b) one or more gene control or regulatory elements, wherein (a) and (b) are operably linked.

14. The sequence of claim 13, wherein the gene (a) comprises the nucleotide sequence of SEQ ID NO:1.

15. A vector comprising the sequence of claim 13.

16. A cell transformed with the sequence of claim 9.

17. The cell of claim 16, wherein the cell is a Gram-positive cocci bacteria.

18. A cell comprising the vector of claim 15.

19. The cell of claim 18, wherein the cell is a Gram-positive cocci bacteria.

20. The cell of claim 18, wherein the cell is *E. coli* BM2973.

21. A monoclonal or polyclonal antibody which specifically binds to the protein of claim 6, and does not specifically bind to the VanA protein or the VanC protein.

22. A monoclonal or polyclonal antibody specific for the protein fragment of claim 7.

23. A kit comprising (a) the antibody of claim 22, and (b) a reagent for detecting an antibody-antigen complex.

24. The kit of claim 23, wherein the antibody is chemically or radioactively labelled.

25. The kit of claim 23, further comprising one or more elements selected from the group consisting of a reagent for lysing a cell, vancomycin, an antibody specific for a VanA protein, and an antibody specific for a VanC protein.

26. The kit of claim 25, wherein the vancomycin is in an aqueous solution.

27. A kit comprising the sequence of claim 11 and one or more elements selected from the group consisting of the nucleotide triphosphates dATP, dCTP, dTTP, and dGTP; a DNA polymerase; and a nucleotide probe specific for a VanA gene or a VanC gene.

28. A method comprising the steps of:
 (a) contacting a sample comprising a DNA sequence with the sequence of claim 11;
 (b) amplifying the DNA sequence to obtain a detectable quantity of amplified DNA; and
 (c) detecting the detectable quantity of amplified DNA.

29. The method of claim 28, wherein the contacting step is hybridizing in the presence of a DNA polymerase and the nucleoside triphosphate dATP, dCTP, dTTP, and dGTP.

30. The method of claim 28, wherein the amplifying step is the polymerase chain reaction (PCR).

31. A method comprising the steps of:
 (a) contacting a sample comprising a DNA sequence with the sequence of claim 11, a nucleotide fragment of a VanA gene, and a nucleotide fragment of a VanB gene, wherein the nucleotide fragment of the VanA gene and the nucleotide fragment of the VanB gene each comprise more than one nucleotide;
 (b) amplifying the DNA sequence to obtain a detectable quantity of amplified DNA; and
 (c) detecting the detectable quantity of amplified DNA.

32. The method of claim 31, wherein the amplifying step is the polymerase chain reaction (PCR).

* * * * *